United States Patent
Cadick et al.

(10) Patent No.: US 9,215,988 B2
(45) Date of Patent: Dec. 22, 2015

(54) LOW POWER TEST SIGNAL GENERATOR FOR MEDICAL EQUIPMENT

(71) Applicant: Medxcel, LLC, Indianapolis, IN (US)

(72) Inventors: Robert Cadick, Indianapolis, IN (US); Dax Hafer, Indianapolis, IN (US)

(73) Assignee: Medxcel, LLC, Indianapolis, IN (US)

( * ) Notice: Subject to any disclaimer, the term of this patent is extended or adjusted under 35 U.S.C. 154(b) by 287 days.

(21) Appl. No.: 13/851,917

(22) Filed: Mar. 27, 2013

(65) Prior Publication Data

US 2014/0298096 A1  Oct. 2, 2014

(51) Int. Cl.
| | |
|---|---|
| G06G 7/58 | (2006.01) |
| A61B 5/0402 | (2006.01) |
| G06F 19/00 | (2011.01) |
| A61B 5/0404 | (2006.01) |

(52) U.S. Cl.
CPC ........ *A61B 5/04021* (2013.01); *G06F 19/3437* (2013.01); *A61B 5/0404* (2013.01)

(58) Field of Classification Search
CPC .. A61B 5/0452; A61B 5/0472; A61B 5/0402; A61B 5/0404; G09F 19/3437; G09F 19/3406
USPC .................... 600/509, 510; 703/11
See application file for complete search history.

(56) References Cited

U.S. PATENT DOCUMENTS

| | | | |
|---|---|---|---|
| 4,204,261 A | 5/1980 | Cook | |
| 4,300,224 A | 11/1981 | Nakazaki | |
| 4,301,512 A | 11/1981 | Keith | |
| 4,736,322 A * | 4/1988 | Clifford | ......................... 703/11 |
| 5,041,973 A | 8/1991 | Lebron | |
| 5,375,105 A | 12/1994 | Borowski | |
| 5,482,472 A | 1/1996 | Garoni | |
| 7,279,906 B2 | 10/2007 | Kay | |
| 7,917,774 B2 | 3/2011 | Ruiter | |

* cited by examiner

*Primary Examiner* — Theodore Stigell
*Assistant Examiner* — Michael Carey
(74) *Attorney, Agent, or Firm* — Maginot, Moore & Beck LLP

(57) ABSTRACT

A cardiac signal generator includes a portable housing, a memory, a processing device, a digital to analog converter, and at least one analog output. The memory stores programming instructions including instructions defining a plurality of mathematical relationships. The processing device is configured to execute the programming instructions to generate a sequence of output values using the plurality of mathematic relationships as a function of time, wherein the sequence of output values defines a sampled waveform output simulating an ECG signal and having linear portions and at least one curved portion. The processing device furthermore provides the sequence of output values at an output. The digital to analog converter is operably coupled to receive the sequence of output values from the output, and generates an electrical signal having a waveform corresponding to the sampled waveform output. The analog output is operably coupled to the digital to analog converter.

21 Claims, 11 Drawing Sheets

100
LOW POWER TEST SIGNAL GENERATOR FOR MEDICAL EQUIPMENT

FIELD OF THE INVENTION

The present invention relates generally to test devices, and more particularly, to devices that simulate ECG signals.

BACKGROUND

ECG equipment includes devices or systems that obtain electrical signals ("ECG signals") representative of electrical signals generated by a patient's heart beat, and provide a visual output of the signal waveform ("ECG waveform"). ECG equipment is useful to medical professionals in detecting anomalies in a patient's ECG waveform caused by abnormal and/or potentially dangerous cardiac conditions. ECG equipment also can detect and display respiration signals generated by the respiratory activity of a patient.

Because of the vital importance of ECG equipment, it is necessary from time to time to test the operation of the equipment. To this end, it is known to provide ECG signal simulators or generators that approximate a human ECG signal. Because the simulated signal has a predetermined heart rate and waveform shape, it may be used to test the ECG equipment. To test the equipment, the leads from the ECG equipment that normally attach to the patient are instead attached to terminals on the ECG signal simulator. The ECG equipment output is then compared to the settings of the ECG signal simulator to ensure that the ECG equipment is properly detecting the heart rate (i.e. pulse), displaying the ECG waveform properly, and/or displaying respiration signals properly.

Moreover, the healthy human heartbeat involves several different signal elements. Accordingly, the ECG waveform associated with a single heartbeat has various regions or features. The ECG signal simulator preferably approximates such features, so that when the ECG equipment is connected to the ECG signal simulator, the ECG equipment output has the visual appearance approximating a human ECG signal.

Accordingly, ECG signal simulators must be capable of generating a signal having multiple features. Moreover, the ECG signal simulator is preferably capable of proving ECG signals at different heart rates (i.e. the frequency at which the ECG waveform repeats). Further, it is preferable if ECG signal simulators can also simulate respiratory signals, at least in a rudimentary manner.

While devices having such capabilities are available on the market, such devices have tended to be large, bulky, and complex. For example, a common design involves storing digital samples forming an ECG waveform. When the device is used, the samples are sequentially retrieved from memory and provided to an analog output, which results in an ECG waveform signal output. One drawback to this design is that in order to store waveforms for multiple heart rates using a sufficient sample rate, the device may need to store thousands of samples. Storing thousands of samples for multiple cardiac waveforms often requires a separate memory device, which can increase cost, weight and power consumption.

It is preferable that such devices be cordless (e.g. battery-operated) to allow for better portability, ease of use, and reduced weight. However, the complex circuitry used for prior art simulators can have relatively high power consumption, which results in reduced battery life and inconvenience. There is a need, therefore, for an ECG signal generator/simulator that has reduced size and power consumption.

SUMMARY

The present invention addresses the above needs, as well as others, by providing a cardiac signal simulator that employs mathematical operations to generate ECG and/or respiratory waveforms, which allows for minimal memory use while still allowing flexibility of heart rate and/or respiratory rate.

A first embodiment comprises a cardiac signal generator that includes memory, a processing device, a digital-to-analog converter (DAC), and one or more analog outputs. The memory stores programming instructions, said programming instructions including instructions defining a plurality of mathematical relationships. The processing device is configured to execute the programming instructions to generate a sequence of output values using the plurality of mathematic relationships as a function of time. The sequence of output values defines a sampled waveform output simulating an ECG signal and having linear portions and at least one curved portion. The processing device is further configured to provide the sequence of output values at an output. The DAC is operably coupled to receive the sequence of output values from the output, and is configured to generate an electrical signal having a waveform corresponding to the sampled waveform output. The analog outputs are operably coupled to the DAC.

The above-described features and advantages, as well as others, will become more readily apparent to those of ordinary skill in the art by reference to the following detailed description and accompanying drawings.

DETAILED DESCRIPTION

Figure 1:
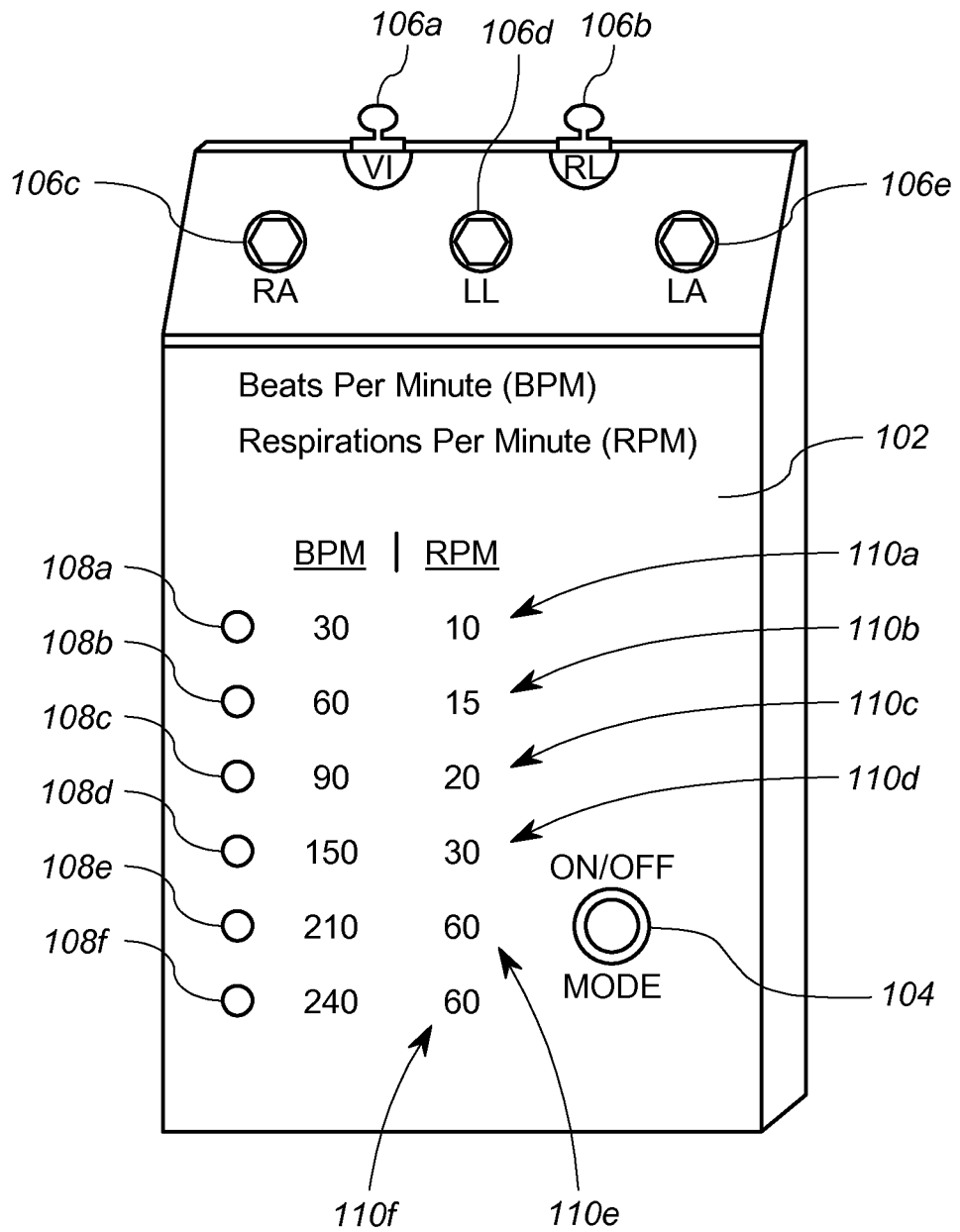
FIG. 1 shows a front plan view of a cardiac simulator according to a first exemplary embodiment of the invention.

FIG. 1 shows a front plan view of a cardiac simulator 100 according to a first exemplary embodiment of the invention. The cardiac simulator 100 includes a housing 102, a user-input 104, a plurality of probe terminals 106a, 106b, . . . 106e, a plurality of indicators 108a, 108b, . . . 108f, and sets of indicia 110a, 110b, . . . 110f.

The housing 102 is a small, portable box that is sized to be held in one hand. The housing 102 encloses circuitry, not shown in FIG. 1, but which is shown in schematic form in FIG. 2. The user input 104 is a push button switch that is disposed and supported in an opening in the housing 102. In this embodiment, the push button switch is open unless in the state of being depressed. The user input 104 includes contacts that form part of the circuitry within the housing 102. As will be discussed below, the single button user input 104 performs all user controlled functions for normal operation. As a consequence, the operation of the cardiac simulator 100 is simplified and intuitive.

The plurality of probe terminals 106a, 106b, . . . 106e comprise connectors configured to receive (and form an electrical connection to) standard ECG monitor leads, not shown. The monitor leads in normal patient operation connect to sensors or electrodes that are attached to different locations on the patient's body, including the chest. For testing purposes, the monitor leads would connect to some or all of the probe terminals 106a, 106b, . . . 106e. In general, the cardiac simulator 100 is configured to provide simulated ECG and respiratory signals at different levels on the probe terminals 106a, 106b, . . . 106e that correspond to expected signal levels in ECG monitors.

Figure 10:
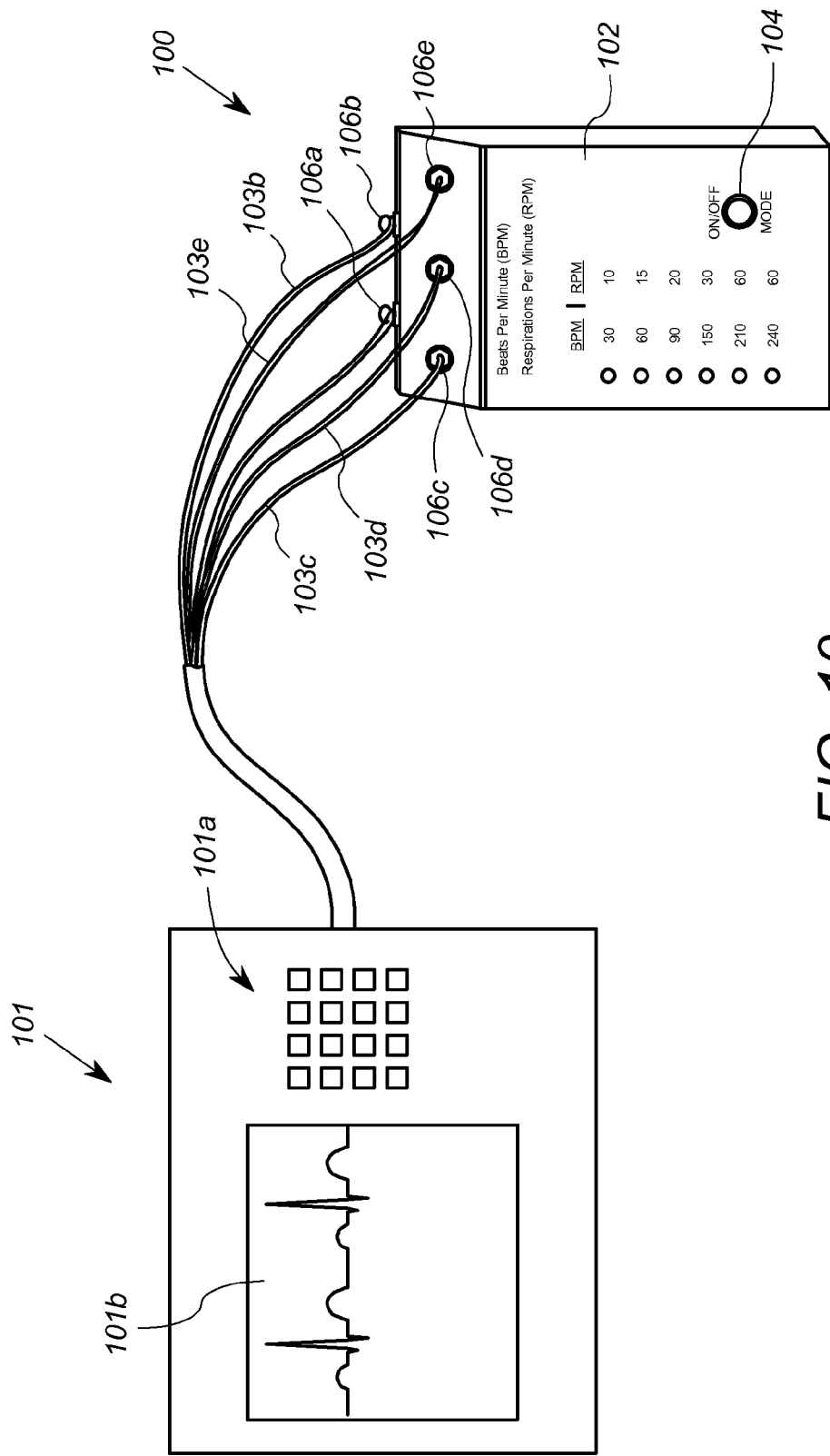
FIG. 10 shows a schematic drawing of the cardiac simulator of FIG. 1 connected to a device under test for testing purposes.

For example, FIG. 10 shows a schematic drawing of the cardiac simulator 100 of FIG. 1 connected to a device under test ("DUT") 101 for testing purposes. The DUT 101 may suitably be any commercially available ECG monitor used to monitor cardiac and respiratory activity in a patient. The DUT 101 typically includes a control panel 101a, a display 101b, and a plurality of probes 103a, 103b, 103c, 103d and 103e. The control panel 101a, as is known in the art, is provided to allow the user to, among other things, control various aspects of the display 101b. The display 101b provides a visual display of, among other things, electrical signals received via the probes 103a-103e. Although not shown in FIG. 10, the probes 103a-103e are configured to be attached to a patient's body, as is known in the art. The DUT 101 may suitably be an Association for Advancement of Medical Instrumentation ("AAMI") standard ECG monitoring device. As such, the DUT 101 includes a brown or V5 probe 103a, a green or RL probe 103b, a white or RA probe 103c, a red or LL probe 103d, and a black or LA probe 103e. In accordance with AAMI standards, these probes 103a, 103b, 103c, 103d and 103e are configured to be applied to predefined portions of a human body, not shown, wherein they can detect changes in impedance caused by cardiac and respiratory activity, in order to generate ECG signals. The DUT 101 causes waveforms representative of the generated ECG signals on the display 101b.

From time to time, it is advantageous and/or necessary to test the DUT 101 to determine whether it is detecting and displaying ECG signals properly. To carry out a test of the DUT 101, the probes 103a-103e are coupled, respectively, to the terminals 106a-106e of the cardiac simulator 100, as shown in FIG. 10. The cardiac simulator 100 then generates simulated ECG signals at the terminals 106a-106e. If the DUT 101 is working properly, then the generated ECG signals will appear on the display 101b.

To this end, as will be discussed below in connection with FIG. 2, the cardiac simulator 100 generates simulated ECG or cardiac signals as a repeating cardiac waveform pattern, each occurrence of the cardiac waveform pattern corresponding to a heartbeat. FIG. 3, discussed further below, shows a timing diagram of an exemplary cardiac waveform 300 representative of a single heartbeat. Referring again to FIG. 1, the cardiac simulator 100 similarly generates respiratory signals as a repeating pattern of a respiration signal. As is known of ECG signals, the respiratory signals are superimposed or modulated on to the cardiac signals.

As will also be discussed below in further detail, the cardiac simulator 100 has six settings or "profiles", each setting having a combination of a predetermined heart-rate and respiratory rate. The "heart-rate" represents the pulse, and more specifically, the frequency with which the cardiac waveform is repeated per minute. The "respiration rate" represents the frequency with which the respiration signal is repeated per minute. Table 1 below shows the six settings or profiles of the embodiment described herein. However, it will be appreciated that other embodiments may use other combinations of heart-rates and respiration rates.

TABLE 1

| Profile | Heart Rate | Respiration Rate |
| --- | --- | --- |
| 1 | 30 | 10 |
| 2 | 60 | 15 |
| 3 | 90 | 20 |
| 4 | 150 | 30 |
| 5 | 210 | 60 |
| 6 | 240 | 60 |

The indicators 108a, 108b, . . . 108f comprise six indicators that correspond to the available profiles of the cardiac simulator 100. Accordingly, because the cardiac simulator 100 in this embodiment has six settings or profiles, the cardiac simulator 100 has six indicators 108a, 108b, . . . 108f. The indicators 108a, 108b, . . . 108f are disposed next to corresponding sets of indicia 110a, 110b, . . . 110f on the housing 102. Each set of indicia 110a, 110b, . . . 110f includes indicia indicative of one of the profiles of the cardiac simulator 100. For example, each set of indicia 110a, 110b, . . . 110f may include two numbers indicating the heart-rate and respiration rate for the corresponding profile.

Each of the indicators 108a, 108b, . . . 108f comprises a single two-state (i.e. on/off) indicator that is disposed next to a corresponding set of indicia 110a, 110b, . . . 110f. The circuitry of the cardiac simulator 100 is configured to use the on-state of the indicators 108a, 108b, . . . 108f to identify the current setting of the cardiac simulator 100. In the embodiment described herein, the indicators 108a, 108b, . . . 108f comprise LED indicators. The use of two-state indicators (and the corresponding indicia) provides the advantage of simplifying the display logic. By contrast, prior art devices include complex, multi-segment LCD displays or other multi-element displays requiring significant amounts of logic. The drivers and logic for such displays can require additional physical footprint and can require additional energy consumption.

In operation, the user depresses the single button user input 104 to start the cardiac simulator 100. The cardiac simulator 100 then starts generating cardiac signals and respiratory signals in accordance with an initial profile. In this embodiment, the initial profile upon start-up is profile 2, because it corresponds to a heart rate and respiratory rate that are in the range of normal. Thus, upon start-up, the second indicator 108b transitions to the actuated state. In some embodiments, the cardiac simulator 100 may continuously "blink" the first indicator 108b to provide more active visual feedback, and to conserve battery power. The other indicators 108a and 108c-108f remain in the unactuated state. If the user depresses the single button user input 104 again, then the cardiac simulator 100 advances to profile 3. In other words, the cardiac simulator 100 generates cardiac signals and respiratory signals in accordance with profile 3, and causes the third indicator 108c to be in the actuated state (and/or blinking on and off). The other indicators 108a, 108b, and 108d-108f are all in the unactuated state. If the user depresses the single button user input 104 yet again, then the cardiac simulator 100 similarly advances to profile 4. In other words, the cardiac simulator 100 generates cardiac signals and respiratory signals in accordance with profile 4, and causes the fourth indicator 108d to be in the actuated state. The other indicators 108a-108c, 108e and 108f are all in the unactuated state. Additional actuation of the single button input device 104 likewise advances the setting of the cardiac simulator 100 to the next setting or profile, with the resulting actuator of the corresponding indicator 108a-108f and the corresponding generation of signals (see Table 1). Thus, the embodiment herein employs a single actuatable user input element to select among various profiles of heart rates and respiration rates. Use of a single actuatable user input element for such purposes simplifies the logic and circuitry footprint, and simplifies user operation.

In addition, as will be discussed further below in detail, the user input 104 may be used to turn the cardiac simulator 100 to the "off" state, where no signals are generated and no indicators 108a-108f are actuated. To this end, when the cardiac simulator 100 is running in steady state, holding the user input 104 for an extended amount of time, for example, two or more seconds, causes the cardiac simulator 100 to go to the "off" state.

Furthermore, in the embodiment discussed herein, the cardiac simulator 100 has an automatic turnoff feature. In particular, if the cardiac simulator 100 does not receive any input signals via the input device 104 for an extended period, such as several minutes or even an hour, the cardiac simulator 100 automatically transitions to the "off" state. This feature helps prevent unintentional prolonged operation that drains battery power. In this embodiment, the automatic turnoff feature can be disabled if, at power up, the input device 104 is held in the actuated state for an extended period, such as 2-5 seconds. In addition, in this embodiment, the cardiac simulator 100 blinks a plurality of the indicators 106a-106f, for example, all of such indicators, when the input device 104 has been held sufficiently long enough for the cardiac simulator 100 to turn off.

Thus, it can be seen that the cardiac simulator 100 of the embodiment described herein provides a flexible and intuitive user interface capable of various operational states, profiles, and commands with a single input device 104 and a few two-state indicators 108a-108f.

Figure 2:
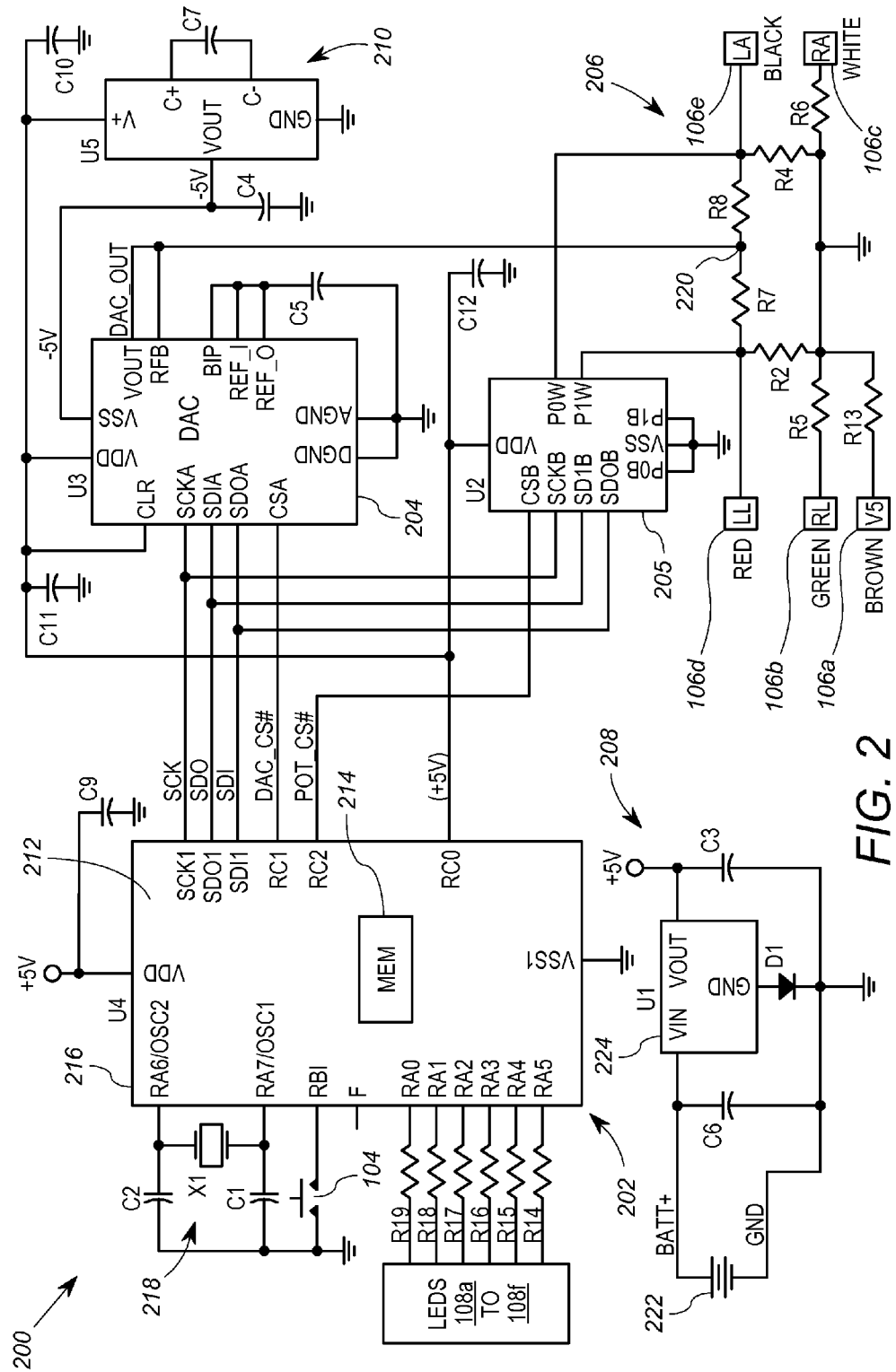
FIG. 2 shows a schematic electrical diagram of the cardiac simulator of FIG. 1.
Figure 3:
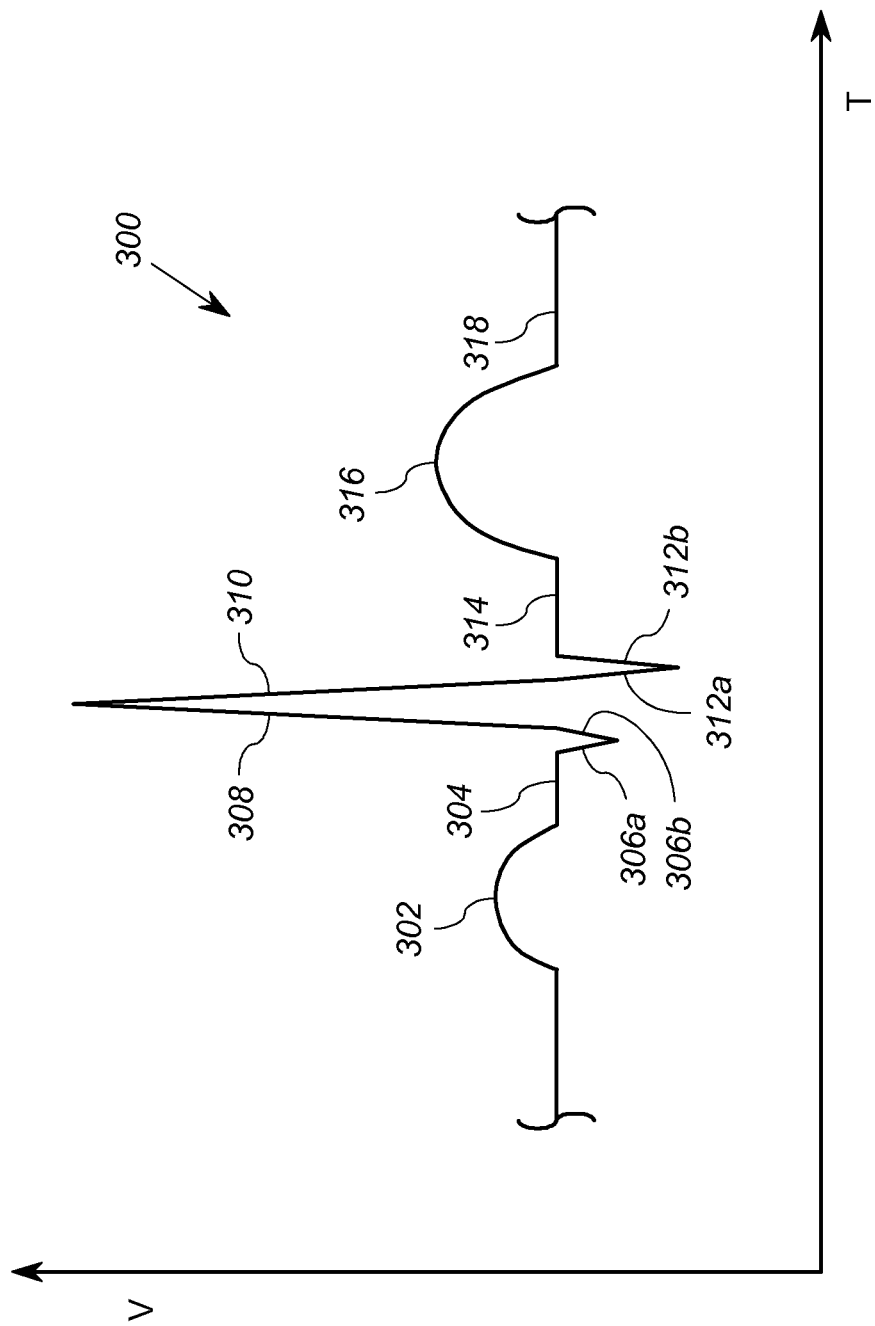
FIG. 3 shows a timing diagram of an ECG signal waveform as a function of time.

FIG. 2 shows a schematic diagram of the electrical components of the exemplary cardiac simulator 100 of FIG. 1.

The cardiac simulator 100 includes a processing circuit 202, a digital-to-analog converter ("DAC") unit 204, a potentiometer 205, an analog output circuit 206, a power supply circuit 208 and a voltage converter 210. The processing circuit 202 includes a processing device 212 and a memory 214 containing programming instructions executed by the processing device 212. In this embodiment, the processing device 212 and memory 214 are disposed within a single integrated circuit chip 216. In this embodiment, the integrated circuit chip 216 is the model PIC18F25K22 microcontroller available from Microchip Technology Inc. However, it will be appreciated that at least some of the advantages of the embodiment described herein may be achieved in embodiments in which a separate memory chip is employed.

In general, the programming instructions within the memory 214 include instructions defining a plurality of mathematical relationships. As will be discussed below, such mathematical relationships define curves that may be combined to form (as a series of digital samples) the standard elements of an ECG waveform, such as that shown in FIG. 3.

The processing device 212 is configured to execute the programming instructions stored in the memory 214 to generate a sequence of output values using the plurality of mathematic relationships as a function of time. The sequence of output values defines a sampled waveform output simulating an ECG signal. As will be discussed below, the generated sample waveform defines both linear portions (i.e. constant slope) and at least one curved portion (changing slope). The processing device 212 is further configured to provide the sequence of output values at an output. The processing device 212 is also operably connected to provide control signals to the indicators 108a-108f, and receive input from the input device 104.

The digital to analog converter (DAC) 204 is operably coupled to receive the sequence of output values from the processing device 212, and to generate an electrical signal having a waveform corresponding to the sampled waveform output. The potentiometer 205 is similarly coupled to receive respiration signals from the processing device 212, and to provide variable resistance connections to the analog output 206 based on the respiration signals. In this embodiment, the variable resistance operates to superimpose a respiration signal pattern on the ECG waveform generated by the DAC 204.

The analog output circuit 206 in this embodiment is a resistor network operably coupled to the DAC 204 and the potentiometer 205 as described above, and is configured to provide ECG test signals to the probe terminals 106a, 106b, . . . 106e with signal levels expected by and/or compatible with normal ECG monitoring equipment.

It will be appreciated that in ECG monitoring, detected ECG signals from the human body typically have both a respiration signal component and a cardiac signal component. It will be appreciated, however, that at least some of the advantages of the embodiment described herein may be achieved even if respiration signals are not superimposed onto the cardiac signals, such that the generated ECG signals contain no respiration component. Accordingly, in this description, ECG signals shall be taken broadly to mean the cardiac signals alone, or the composite of the cardiac signal and the respiration signal.

Referring again to FIG. 2, the circuitry of the cardiac simulator 100 of this exemplary embodiment is described in further detail. The processing device 212 includes several inputs and outputs formed as pins on the integrated circuit chip 216. In particular, the processing device 212 includes LED outputs RA0-RA5, oscillator circuit pins OSC1, OSC2, serial data ports SCK, SDI, SDO, a first chip select port RC1, a second chip select port RC2, button detect input RB1, and a bias voltage output RC0. It will be appreciated that the processing device 212 also includes other inputs and outputs that may be used for calibration, programming and the like.

As discussed above, the processing device 212 and the memory 214 are embodied in a Model PIC18F25K22 Microcontroller available from Microchip Technology Inc. One of the advantages of the embodiment described herein is that the method of generating ECG signals requires little memory, and thus the entire device may be programmed and operated in the 16K flash memory, which forms at least part of the memory 214, that is inherent with the in integrated circuit chip 216. Other devices that employ large amounts of stored data representative of cardiac signal waveforms require much more data storage, and require significant memory external to the integrated circuit chip 216, and/or a larger and more expensive integrated circuit chip.

In addition to the processing device 212 and memory 214, the processing circuit 202 includes an oscillator circuit 218. The oscillator circuit 218 includes a 20 MHz crystal resonator X1 and capacitors C1, C2 coupled in a conventional manner to form an external oscillator circuit for a processor. In particular, the capacitor C1, which may suitably be a 22 pF capacitor, is serially coupled between the oscillator circuit pin OSC1 and ground, and the capacitor C2, which has the same capacitance as the capacitor C1, is serially coupled between the oscillator pin OSC2 and ground. The crystal resonator X1 is coupled across the pins OSC1, OSC2.

The DAC 204 is a device configured to receive digital signals and generate an analog output therefrom. The DAC 204 is configured to generate analog output signals within a voltage range that, when provided through the analog output circuit 206, generate signal levels compatible with standard ECG monitoring equipment. Accordingly, in this embodiment, the DAC 204 provides output signals approximately between −2 volts and 2 volts. The level of the output signals of the DAC 204 is a function of the input digital value.

The DAC 204 may suitably be embodied as a model MAX504 digital-to-analog converter available from Maxim Integrated Products, Inc. The DAC 204 includes a chip select input CSA, a serial clock input SCKA, a serial data input SDIA, a serial data output SDOA, a high voltage input VDD, a low voltage input VSS, a DAC output VOUT, and ground pin DGND. The DAC 204 may suitably have other inputs and outputs that would be connected in a conventional manner. In this embodiment, the DAC 204 is configured, upon receiving a chip enable signal on the chip select input CSA, to receive serial data in the input SDIA. The DAC 204 is further configured to provide an output signal having a voltage level that is in the range between a voltage received on the low voltage input VSS and a voltage received on the high voltage input VDD. In this particular embodiment, the range of output voltages (−2 volts to 2 volts) is defined in part by a reference voltage Vdref, which in the embodiment described herein is set to two volts. The DAC 204 in this embodiment is set to have an output voltage range from −Vdref to +Vdref. The voltage level of the output signal is proportional to the received serial data value within the defined range. Stated another way the DAC output voltage may be expressed as $$V\_out = dig\_val/dig\_range(2Vdref) - Vdref, \quad (1)$$

where V_out is the output analog voltage provided at VOUT, Vdref is the reference value of the DAC 204, dig_val is the digital value received at the serial input SDIA, and dig_range is the range of values of the DAC 204.

The serial clock input SCKA of the DAC 204 is operably coupled to the pin SCK of the processing device 212. The serial data input SDIA is operably coupled to the serial data output pin SDO of the processing device 212, and the serial data output SDOA is operably coupled to the serial data input pin SDI of the processing device 212. The chip select input CSA of the DAC 204 is operably coupled to the chip select output RC1 of the processing device 212. The high voltage input VDD is coupled to the bias output RCO of the processing device 212, and the low voltage input VSS is coupled to the voltage converter 210, as will be discussed further below.

The potentiometer 205 is a device configured to receive digital signals, and provide connections having a variable resistance value that corresponds to the received digital signals. Accordingly, in this embodiment, the potentiometer 205 provides two different resistances (with different connections), each controllable by a different digital value. Each controllable resistance is a function of the input digital value.

The potentiometer 205 may suitably be embodied as a model MCP4252 digital potentiometer available from Microchip Technology, Inc. The potentiometer 205 includes a chip select input CSB, a serial clock input SCKB, a serial data input SDIB, a serial data output SDOB, a bias voltage input VDD, a first output POW, a second output P1W, and reference connections P0B, P1B. The potentiometer 205 may suitably have other inputs and outputs that would be connected in a conventional manner. In this embodiment, the potentiometer 205 is configured, upon receiving a chip enable signal on the chip select input CSB, to receive first and second data values via the serial data input SDIB. The potentiometer 205 is further configured to provide a resistance between the output P0W and the connection P0B that is proportional to the first data value. Similarly, the potentiometer 205 is further configured to provide a resistance between the output P1W and the connection P1B that is proportional to the second data value. The resistances and data values are selected to correspond to the variance in cardiac signals (as generated by the DAC 204) that occurs with normal respiratory signals. These resistances are also selected in light of the analog circuit 206. In the embodiment described herein, the resistance between P0W and P0B can vary between 7535 and 5778 ohms, and the resistance between P1W and P1B can vary between 7535 and 5778 ohms. It will be appreciated that the exact level of the variable resistance will depend upon the circuitry employed in the analog output circuit 206. In general, the potentiometer 205 should vary the output resistance via the analog output circuit 206 on the order of three ohms.

The serial clock input SCKB of the potentiometer 205 is operably coupled to the pin SCK of the processing device 212. The serial data input SDIB is operably coupled to the serial data output pin SDO of the processing device 212, and the serial data output SDOB is operably coupled to the serial data input pin SDI of the processing device 212. The chip select input CSB of the potentiometer 205 is operably coupled to the chip select output RC1 of the processing device 212. The high voltage input VDD is coupled to the bias output RCO of the processing device 212, and the low voltage input VSS is coupled to ground.

As discussed above, the analog output circuit 206 is a circuit that provides the ECG signal output of the cardiac simulator 100 on or across pairs of the probe terminals 106a-106e. In the embodiment described herein, the analog output 206 provides the ECG signal based on the output signal from the DAC 204, as modulated by the variable resistance of the potentiometer 205. The analog output circuit 206 includes a resistive network to provide outputs at various levels across pairs of the probe terminals 106a-106e.

To this end, in the embodiment described herein, the analog output circuit 206 has a first input 220 operably connected to receive the output cardiac signal from the output VOUT of the DAC 204. A first resistor R7 (249 k-ohms) is connected between the input 220 and the probe terminal 106d. A second resistor R8 (360 k-ohms) is connected between the input 220 and the probe terminal 106e. A third resistor R2 (261 ohms) is coupled between the terminal 106d and ground. A fourth resistor R4 (261 ohms) is coupled between the probe terminal 106e and ground. A fifth resistor R (249 ohms) is coupled between the terminal 106b and ground. A sixth resistor R6 (249 ohms) is coupled between the probe terminal 106c and ground. A seventh resistor R13 is couple between the probe terminal 106a and ground.

In this configuration, it will be appreciated that probes of a normal ECG monitor to be tested (e.g. the DUT 101 of FIG. 10) can be coupled in a standard way to the probe terminals 106a-106e. FIG. 10, discussed above, describes the conventional way of connecting an exemplary ECG monitor to the probe terminals 106a-106e.

In this embodiment, the power supply 208 includes a battery 222, a voltage regulator 224, a capacitors C3, C6 (both having a capacitance of 1 μF), and a diode D1. The battery 222 is preferably a 9 volt battery, which allows the device to be light weight while still powering the logic voltage levels of the various digital circuit components. The voltage regulator 224 is a device having an input VIN configured to receive the output voltage of the battery 222 and configured to provide a regulated 5 volt DC output at an output VOUT. The voltage regulator 224 also has a ground connection GND. Such voltage regulators are conventional. In this embodiment, the voltage regulator 224 may suitably be a model MCP1702-5002E/MB voltage regulator available from Microchip Technologies, Inc.

As shown in FIG. 2, the positive terminal of the battery 222 is coupled to the voltage regulator input VIN, and the negative terminal of the battery 222 is coupled to and/or defines circuitry ground. The capacitor C6 is coupled between the regulator input VIN and ground, and the capacitor C3 is coupled between the regulator output VOUT and ground. The capacitors C3 and C6 may both suitably be 1 µf. The diode D1 is coupled in a forward biased manner between the regulator ground connection GND and circuit ground. The voltage regulator output VOUT is coupled to provide the 5 volt DC output to bias connection VDD of the processing device 212. It will be appreciated that all other devices receive the 5 volt DC bias voltage from the output RC0 of the processing device 212. In this manner, the processing device 212 can control whether the other devices are powered, which is advantageous to put the cardiac simulator 100 in an extremely low power sleep mode.

As discussed above, the voltage converter 210 is a device that is configured to generate a negative bias voltage so that the DAC 204 is capable of generating output analog signals that range from −5 volts to +5 volts. To this end, the voltage converter 210 may suitably be a charge pump converter device, such as the model TC7660 voltage converter available from Microchip Technologies, Inc. The voltage converter 204 in this embodiment has a supply voltage input V+, a negative voltage output VOUT, capacitor connections C+, C−, and a ground connection GND. The supply voltage input V+ is coupled to the RC0 output of the processing device 212. The negative voltage output VOUT is coupled to the VSS input of the DAC 204. A 10 µF capacitor C7 is coupled between the capacitor connections C+, C−, and the ground connection GND is coupled to circuit ground.

In the general operation of the cardiac simulator 100, the rest or sleep mode is an ultra low power mode of the processing device 212. In the sleep mode, the processing device 212 receives bias voltage from the power supply 208 at the input VDD. However, the processing device 212 holds the output RC0 at 0 volts. Accordingly, the output RC0 does not provide bias operating voltage to any of the voltage converter 210, the DAC 204, or the potentiometer 205. The processing device 212 likewise does not provide any other output signals. As a consequence, no voltage signals appear on the probe terminals 106a-106e, and none of the indicators 108a-108f are illuminated. In the sleep mode, the processing device 212 only monitors for depression of the input device 104, which indicates that the user wants the cardiac simulator 100 to transition to the active mode.

In general, upon detecting the depression of the input device 104, the processing device 212 enters the active mode, which includes initiating clocks and counters within the processing device 212. The processing device 212 thereafter executes software instructions stored in the memory 214 to carry out the processes described below, and described in further detail in connection with FIGS. 4-9.

In general, the processing device 212 first starts operating in an initial profile, such as, for example, the second profile identified in Table 1, which corresponds to a setting of 60 heart beats and 15 respirations per minute. The processing device 212 remains that profile until it detects another depression of the input device 104. If the processing device 212 detects another such depression of the input device 104, then the processing device 212 proceeds to start operating in the next profile according to Table 1. Thus, for example, if the current setting is the second profile of Table 1 (60/15), then the processing device 212 would advance to the third profile (90/20). If the current profile is the last profile 6, then the processing device 212 would return to the first profile, profile 1, if the input device 104 is depressed.

The processing device 212 thereafter generates a digital cardiac signal and a digital respiration output signal. The digital cardiac signal is a sequence of output values that form sampled version of the ECG waveform, in a repeating pattern. Thus, the sample values of the digital cardiac signal correspond to the voltage levels of the ECG waveform 300 of FIG. 3. The sample frequency is 1000 samples per second.

In accordance with the embodiment of the invention described herein, the processing device 212 generates the digital cardiac signal using the plurality of mathematic relationships as a function of time. As shown in FIG. 3, the ECG waveform may be divided into various segments including the P-wave 302, the PQ rest 304, the Q-wave 306a, 306b, the R-wave up slope 308, the R-wave down slope 310, the S-wave 312a, 312b, the ST rest 314, T-wave 316 and the end rest 318. In this embodiment, the processing device 212 uses various relationships as a function of time to create the samples (series of discrete digital values) that form the various segments 302-316.

Moreover, the processing device 212 generates the entire digital ECG waveform such that it repeats at a frequency that corresponds to the heart rate of the current "profile". Thus, if the processing device 212 is currently in the third profile, which corresponds to a heart rate of 90, then the processing device 212 generates the processing digital ECG waveform (i.e. the digital sampled version of the ECG waveform 300 of FIG. 3) ninety times per minute. If the processing device 212, however, is currently in the second setting, then the processing device generates the digital ECG waveform sixty times per minute. It will be noted that the length or duration of the ECG waveform necessary is different for different heart rates. For example, the duration of the ECG waveform 300 at a heart rate of sixty will be one second, while the duration of the ECG waveform 300 at a heart rate of ninety will be 0.667 seconds. The processing device 212 generates the digital ECG waveform having variable durations by varying the duration of at least one of the segments 302-316. To achieve the six different heart rates of the six profiles of Table 1, the processing device 212 varies the duration of multiple segments 302-316, as illustrated in Table 2, discussed below. Please note that in Table 2, the Q-down slope 306, the QR up slope 308, the RS down slope 310, the S up slope 312 are grouped together as a single "QRS segment".

TABLE 2

| Setting | P-wave | PQ-rest | QRS | ST-rst | T | End Rst |
|---|---|---|---|---|---|---|
| 1 | 120 | 60 | 80 | 80 | 160 | 1500 |
| 2 | 120 | 60 | 80 | 80 | 160 | 500 |
| 3 | 120 | 60 | 80 | 80 | 160 | 167 |
| 4 | 30 | 20 | 80 | 50 | 60 | 160 |
| 5 | 30 | 20 | 80 | 50 | 60 | 46 |
| 6 | 30 | 20 | 80 | 50 | 60 | 10 |

As will be discussed below in connection with FIGS. 8A and 8B, the digital ECG waveform has linear portions (corresponding to segments 304, 306, 308, 310, 312, 314 and 318, and curved portions (corresponding to segments 302 and 316). By curved, it is meant the relationship of sampled output value to time is not linear for the segment, as is the case for the T-wave and the P-wave.

In general, the processing device 212 generates the digital cardiac signal by providing the sequence of values representative of the repeating digital ECG waveform on the serial data output SDO. The processing device 212 further operates to write each value to the DAC 204 by providing an enable signal on the DAC chip select output RC1 whenever a new value of the sequence of values is available.

In addition to generating the digital cardiac signal, the processing device 212 further generates output signals representative of a respiration signal. To this end, the processing device 212 generates a repeating sequence of values corresponding to a time varying respiration signal. The sequence repeats at a rate corresponding to the respiration rate for the current profile as shown in Table 1. The processing device 212 provides the digital respiration signals on the serial data output SDO. However, to write the respiration signals to the potentiometer, the processing device 212 provide an enable signal on the chip select output RC2.

Furthermore, it will be appreciated that the processing device 212 further causes the indicator 108x that corresponds to the current setting x of Table 1 to be energized or illuminated. To this end, the outputs RA0-RA5 of the processing device 212 are operably coupled to the indicators 108a-108f. The indicators 108a-108f are further coupled to ground, such that positive voltage received on any of the outputs RA0-RA5 will cause the corresponding indicator 108a-108f to illuminate. In this embodiment, the processing device 212 causes the corresponding indicator 108a-108f to intermittently illuminate (i.e. blink) at a rate equivalent to the heart rate. This feature provides extra feedback to the user as to the heart rate and conserves battery power.

In any event, the DAC circuit 204 receives the sequence of digital values representative of the cardiac signal from the processing device 212 and converts the signals to into a continuous analog signal having a voltage level that corresponds to the digital values. The DAC circuit 204 further receives at its VDD input the +5 volt DC signal from the output RC0 of the processing device 212. The DAC circuit 204 also receives at its VSS input the −5 volt DC signal from the output VOUT of the voltage converter 210. As discussed above, the DAC 204 provides an output signal within a range defined by a reference voltage, Vdref, set at 2 volts, and ranging from approximately a low voltage of −Vdref to approximately a high voltage +Vdref. Preferably the output voltage (as measured from the voltage at −Vdref) is proportional to the received digital value.

More specifically, each time the DAC 204 receives an enable signal at its chip select input CSA, the DAC 204 obtains a value at its serial data input SDIA from the processing device 212. The DAC 204 then converts the signal to voltage value V_out that is equal to:

$$V\_out = dig\_val/dig\_range(2Vdref) - Vdref, \quad (1)$$

where dig_val is equal to the received digital value, and dig_range is the maximum possible digital value in the DAC 204. As discussed above, the DAC 204 receives digital values of the ECG waveform sequence at approximately every 1 millisecond.

Referring to the examples of FIG. 3, the DAC 204 may suitably receive digital values corresponding to the ECG waveform 300 of FIG. 3 at its serial data input SDIA and generate an analog signal having the ECG waveform 300 shown in FIG. 3 at its output VOUT.

In a similar manner, the potentiometer 205 receives the sequence of digital values representative of the respiration signal from the processing device 212 and converts the signals into variable resistances between the input POW and ground, and between the input P1W and ground. The resistances correspond to the received digital values. More specifically, the resistances provided by the potentiometer 205 are proportional to the received digital values. As with the DAC 204, the potentiometer 205 only receives values at its serial data input SDIB when it receives an enable signal at its chip select input CSB.

The analog output circuit 206 receives the analog output (cardiac signal) at the input node 220. The analog output circuit 206 provides the cardiac signal at different levels between different probe terminals 106a-106e. For example, the output signal will have one level as measured from terminal node 106d to any of terminal nodes 106a, 106b, 106c, and another level as measured from the terminal node 106e to any of terminal nodes 106a, 106b and 106c. Furthermore, the variable resistance of the potentiometer 105 amplitude modulates the output cardiac signal by varying the output resistance between the terminals 106d and 106e and ground, parallel to the ground paths through R2 and R4.

As a result, the output signal is a cardiac signal having a repeating ECG waveform similar to that of FIG. 3, with a low frequency amplitude modulation superimposed on top, which corresponds to the respiration waveform.

In use, ECG equipment under test, not shown, receives such signals at varying levels by connecting the probes of such equipment to the probe terminals 106a-106e. The ECG equipment then displays and otherwise monitors or processes the signals and generates output, as if connected to a patient. A technician may then compare the signal as displayed or processed on the ECG equipment to the known output heart rate and respiration rate from the profile x of the cardiac simulator 100. The technician obtains the expected heart rate and respiration rate by observing the illuminated one of the LEDs 108$_x$ corresponding to the profile x, and the indicia 110x disposed adjacent the illuminated LED 108x. Moreover, the technician may observe whether the ECG equipment output shows the various portions of the ECG waveform 300 of FIG. 3 in a predictable manner.

One of the benefits of the cardiac simulator 100 described above is its simplicity of use. Instead of complex data entry to identify a specific heart rate and respiration rate, the cardiac simulator 100 of FIG. 1 has six predetermined combinations of heart rate and respiration rate, which may be selected by the user simply by repetitive actuation of the single key input device 104. The LED indicators 108a-108f (and indicia 110a-110f) provide immediate identification of the current setting of the device, thereby also simplifying use. Moreover, such an elegantly efficient display requires little power and processing circuitry.

Another advantage of the embodiment of FIGS. 1 and 2 is the use of output values for the ECG waveform (and respiration waveform) that are generated mathematically, by a plurality of equations (both linear and non-linear). By contrast, prior art devices that store values for entire waveform patterns (i.e. where each sample value is stored in a memory and retrieved in sequence during operation) require more memory. Such devices further require external memory reads which can increase overall power consumption.

Figure 4:
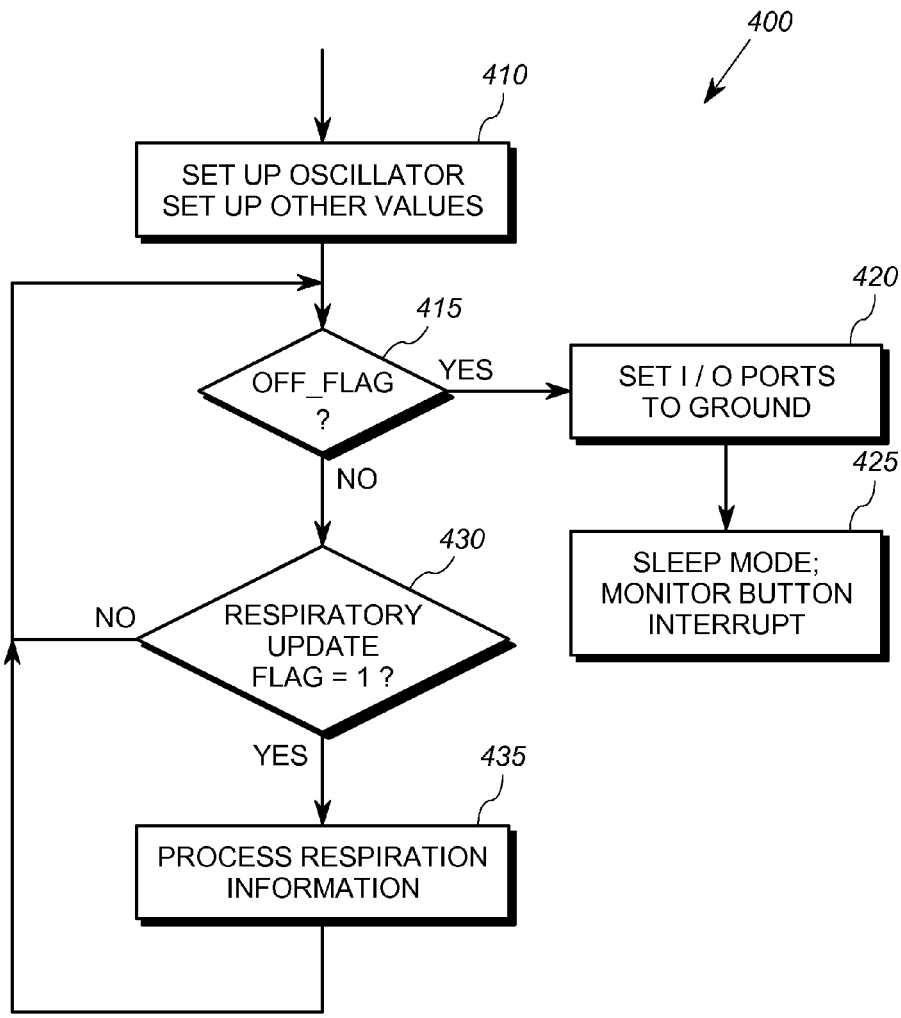
FIG. 4 shows a flow diagram of an exemplary computer program executed by the processing device of the cardiac simulator of FIG. 1.
Figure 4:
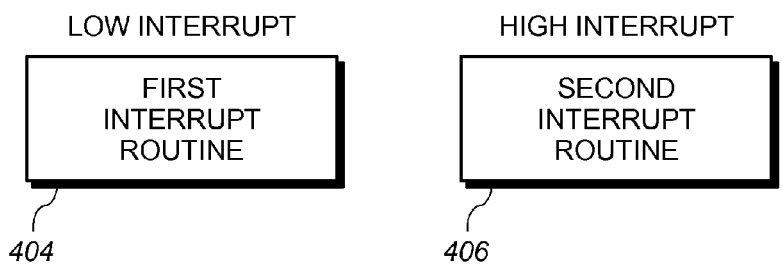

FIGS. 4-9 show in further detail the operation of the processing device 212 to carry out the functions described above. In particular, FIG. 4 shows a flow diagram of the general computer program 400 executed by the processing device 212. The computer program 400 is stored in the memory 214.

The computer program 400 in this embodiment includes a main flow 502, a first interrupt routine 404, and a second interrupt routine 406. In general, when the processing device 212 is active (i.e. not in the sleep mode or off state), the processing device 212 executes the main flow 402 until it receives an interrupt. If a first interrupt is received, then the processing device 212 exits the main flow 402 and executes the first interrupt routine 404. If a second interrupt is received, then the processing device 212 exits the main flow 402 and executes the second interrupt routine 406. Upon completing either of the interrupt routines 404, 406, the processing device 212 returns to the main flow 402 until the next interrupt is received.

Referring now to the main flow 402, the processing device 212 executes the first step 410 upon power up, or in other words, when processing device 212 enters the active mode (when the cardiac monitor 100 is turned on). As discussed above, the processing device 212 enters the active mode when, during the sleep mode, the processing device 212 detects actuation of the input device 104. In step 410, the processing device 212 sets up the oscillator and sets up other values, including timing values, used in the normal operation of the processing device 212. The processing device 212 thereafter executes step 515. The processing device 212 also provides a high logic (e.g. 5 volt) signal on its output RC0, thereby providing bias/operating power to the DAC 204, the voltage converter 210 and the potentiometer 205.

In step 415, the processing device 212 determines whether a flag off_flag is set. As will be discussed below, the off_flag is set (within the second interrupt routine 406) upon detection of a long-held actuation of the input device 104. If the off_flag is set, then the processing device 212 proceeds to step 420 to start operations to enter the sleep mode. If the off_flag is not set, then the processing device 212 proceeds to step 430.

To enter the sleep mode, the processing device 212 in step 420 sets all outputs to ground, thereby extinguishing any indicators 108a-108f, and also removing the voltage from the output RC0. The removal of voltage from the output RC0 removes bias/operating power from the DAC 204, the voltage converter 210 and the potentiometer 205. The processing device 212 thereafter proceeds to step 425. In step 425, the processing device 212 enters the sleep mode, thereby stopping virtually all operations except for monitoring for actuation of the input device 104. As discussed above, in the sleep mode, the processing device 212 performs virtually no operations, thereby consuming little or no energy, and merely transitions to an on-state or active mode when the input device 104 is actuated, thereby completing a circuit to at least one input of the processing device 212.

However, if the off_flag is not set in step 415, as discussed above, then the processing device 212 executes step 430. In step 430, the processing device 212 determines whether it is time for updating the respiration signal, or in other words, whether the flag resp_update is set to 1. If not, then the processing device 212 returns to step 415 and proceeds accordingly, subject to the first and second interrupt routines as per the normal operation. If, however, the flag resp_update is set, then the processing device 212 proceeds to step 435.

Figure 9:
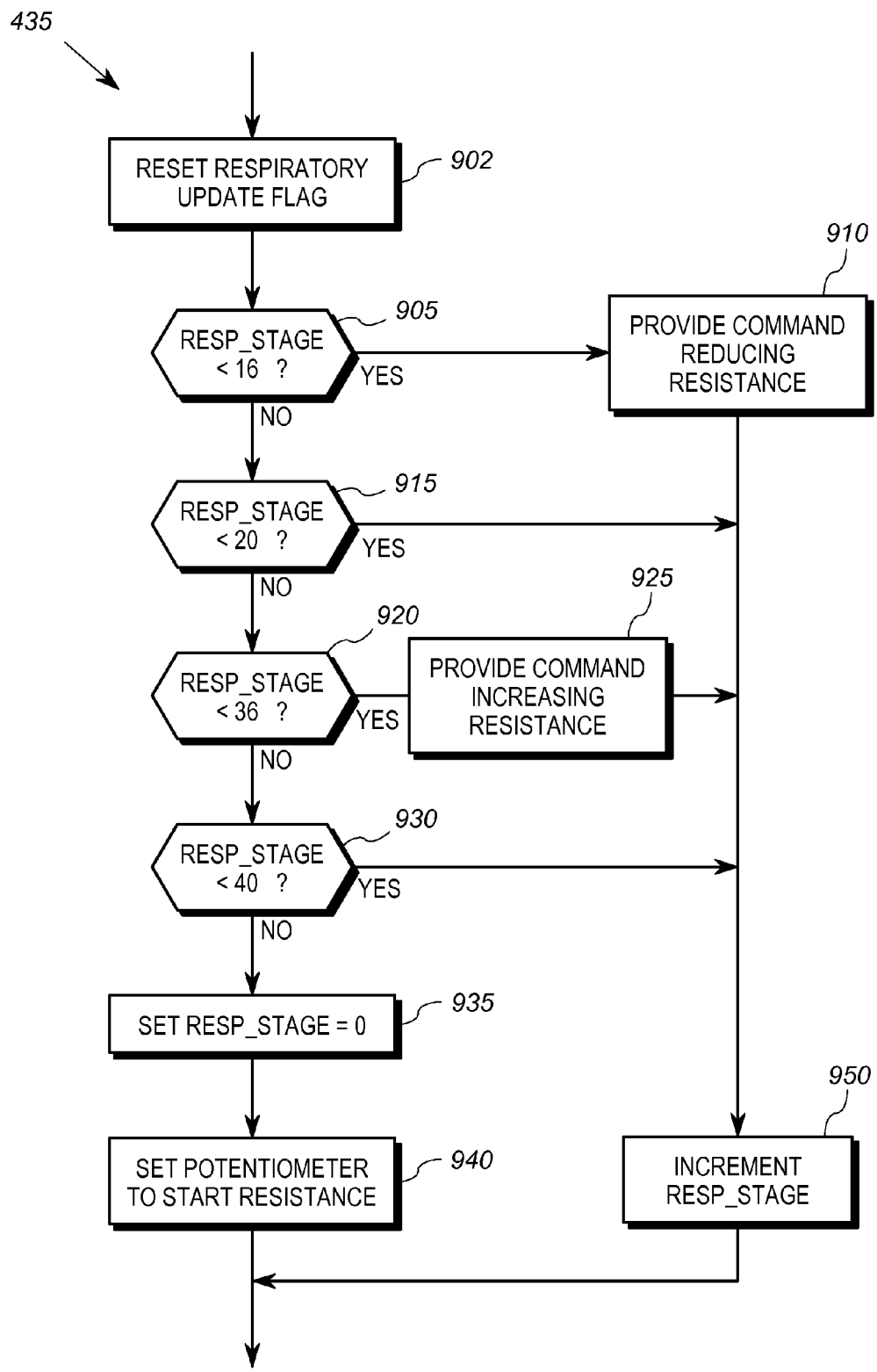
FIG. 9 shows a flow diagram of an exemplary respiration output update routine of FIG. 4.

In step 435, the processing device 212 updates the digital respiration signal and provides the digital respiration signal to the potentiometer 205 via serial data communications as discussed above in connection with FIG. 2. FIG. 9, discussed further below, provides a more detailed flow diagram of the operations of step 435 that update the respiration signal. After updating the respiration signal, the processing device 212 returns to step 415 to proceed accordingly.

The first interrupt routine 404 is a routine that the processing device 212 executes when a first interrupt signal is received. In this embodiment, the first interrupt signal is tied to the input that receives a signal when the input device 104 is actuated. Accordingly, whenever the processing device 212 is in the active mode (i.e. not the sleep mode of step 425), the processing device 212 performs the operations of the first interrupt routine 404 every time the input device 104 is actuated (i.e. the push-button is pressed). In general, the first interrupt routine 404 includes advancing the current profile (see Table 1) to the next profile. Changing the profile or setting includes defining the appropriate time limits for each stage of the ECG cardiac waveform (as per Table 2), and setting the appropriate time limits for the respiration signal (as per Table 1). The actual time limit values may suitably be in terms of milliseconds.

Figure 5:
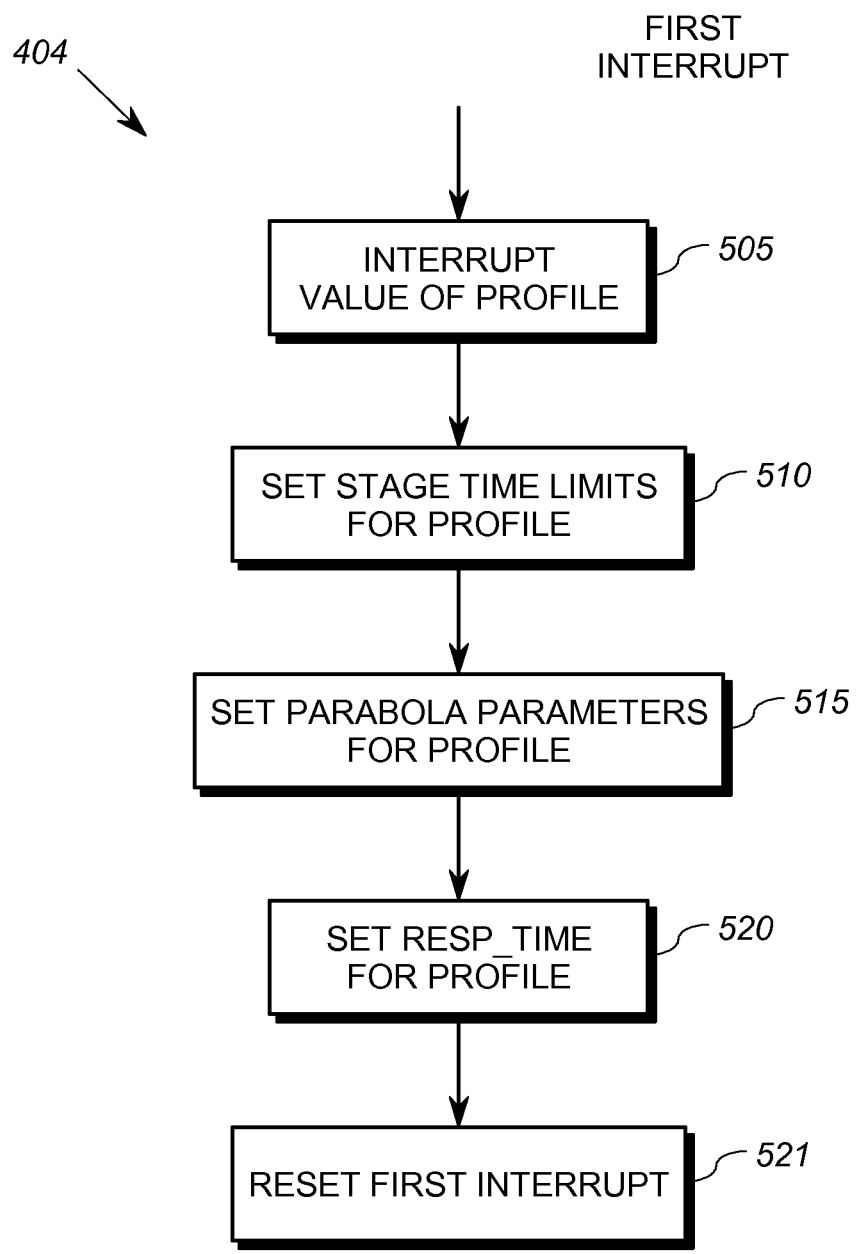
FIG. 5 shows a flow diagram of an exemplary first interrupt routine of the computer program of FIG. 4.

FIG. 5 shows the operations of the first interrupt routine 404 in further detail. In particular, in step 505, the processing device 212 identifies the value profile equal to the current profile or setting plus one. The value profile represents the identity of the current profile (see Table 1). Thus, if profile=3 (i.e. the current setting is 3) prior to step 505, then the processing device 212 sets the value profile=4 after execution of step 505. As shown in Table 1, the setting or profile 4 corresponds to a heart rate of 150 beats/minute (BPM) and a respiration rate of 30 respirations per minute (RPM). In any event, once the value of profile is updated, the processing device 212 executes step 510.

In step 510, the processing device 212 sets the time limits for the various stages of the ECG waveform in accordance with the new profile or setting value, profile. In general, the time limit for each of the stages P-wave, PQ-rest, QRS complex, ST-rest, T-wave and End Rest are based on the time limits of Table 2. In this embodiment, the P-wave, PQ-rest, ST-rest, T-Wave and End Rest each comprise one of stages, and the QRS complex is divided into six different stages. Table 3, provided below, identifies each stage, its duration, and its corresponding portion of the waveform of FIG. 3.

TABLE 3

| Stage | Duration | Waveform (FIG. 3) |
| --- | --- | --- |
| Stage 1 | P-wave$_x$ | 302 |
| Stage 2 | PQ-rest$_x$ | 304 |
| Stage 3 | QRS-complex$_x$/8 | 306a |
| Stage 4 | QRS-complex$_x$/8 | 306b |
| Stage 5 | QRS-complex$_x$/4 | 308 |
| Stage 6 | QRS-complex$_x$/4 | 310 |
| Stage 7 | QRS-complex$_x$/8 | 312a |
| Stage 8 | QRS-complex$_x$/8 | 312b |
| Stage 9 | ST-rest$_x$ | 314 |
| Stage 10 | T-wave$_x$ | 316 |
| Stage 11 | End-rest$_x$ | 318 | where P-Wave$_x$ is the P-Wave value of Table 2 for the profile x, the value PQ-Rest$_x$ is the PQ-Rest value of Table 2 for the profile x, the value QRS$_x$ is the QRS value of Table 2 for the profile x, the value ST-Rest$_x$ is the ST-Rest value of Table 2 for the profile x, the value T-Wave$_x$ is the T-Wave value of Table 2 for the profile x, and End-Rest$_x$ is the End-Rest value of Table 2 for the profile x.

Accordingly, in step 515, the processing device 212 determines the cumulative time limits for each stage for the current profile x using the following relationships.

Stage_1=P-Wave$_x$

Stage_2=Stage_1+PQ-Rest$_x$

Stage_3=Stage_2+$QRS$-complex$_x$/8;

Stage_4=Stage_3+$QRS$-complex$_x$/8;

Stage_5=Stage_4+$QRS$-complex$_x$/4;

Stage_6=Stage_5+$QRS$-complex$_x$/4;

Stage_7=Stage_6+$QRS$-complex$_x$/8;

Stage_8=Stage_7+$QRS$-complex$_x$/8;

Stage_9=Stage_8+$ST$-Rest$_x$

Stage_10=Stage_9+$T$-Wave$_x$

Stage_11=Stage_10+End-Rest$_x$

Thus, for example, in the profile 2, the time limit values are as follows:

Stage_1=120 (End of $P$-Wave)

Stage_2=120+60=180 (End of $PQ$-Rest end)

Stage_3=180+80/8=190

Stage_4=190+80/8=200

Stage_5=200+80/4=220

Stage_6=220+80/4=240

Stage_7=240+80/8=250

Stage_8=250+80/8=260 (End of $QRS$ complex)

Stage_9=260+80=340 (End of $ST$-Rest)

Stage_10=340+160=500 (End of $T$-Wave)

Stage_11=500+500=1000 (End of End-rest and $ECG$ waveform)

In addition to generate the time limits or counter limits for the eleven defined stages, the processing device 212 in step 515 generates parameters for the P-wave and T-wave curved segments of the ECG waveform. Specifically, the processing defines a value HPW, which is one-half of the duration of the P-Wave (P-Wave$_x$/2), and HTW, which is one-half of the value of the T-Wave (T-Wave$_x$/2). The processing device 212 thereafter performs step 620.

In step 520, the processing device 212 sets the value resp_time equal to the respiratory period for the current value of profile. In this embodiment, the value of resp_time is equal to the respiratory period in milliseconds. To this end, the value of resp_time for a setting x is set equal to:

resp_time=(60,000/resp_freq$_x$)/stages, where resp_freq$_x$ is the respiration frequency from the Table 1 for a setting x, and stages is a constant value representing the number of individual updates to the digital respiration signal that are made in one respiration cycle. In this embodiment, stages=40.

Thereafter, in step 525, the processing device 212 resets the first interrupt and returns to the execution of the main flow 402 of FIG. 5. Accordingly, the main purpose of the first interrupt routine 404 is to process the input from the input device 104 to change the setting or profile, and the various parameters associated with the new profile.

Referring again to FIG. 4, the second interrupt routine 406 is timer-based, and is executed every 1 millisecond in this embodiment. In general, each execution of the second interrupt routine 406 generates one of the sequence of values that from the digital ECG signal. The second interrupt routine 406 also monitors for prolonged actuation of the input device 104, and manages the respiratory signal update flag resp_update. The second interrupt routine 406 is described in further detail below in connection with FIG. 6.

Figure 6:
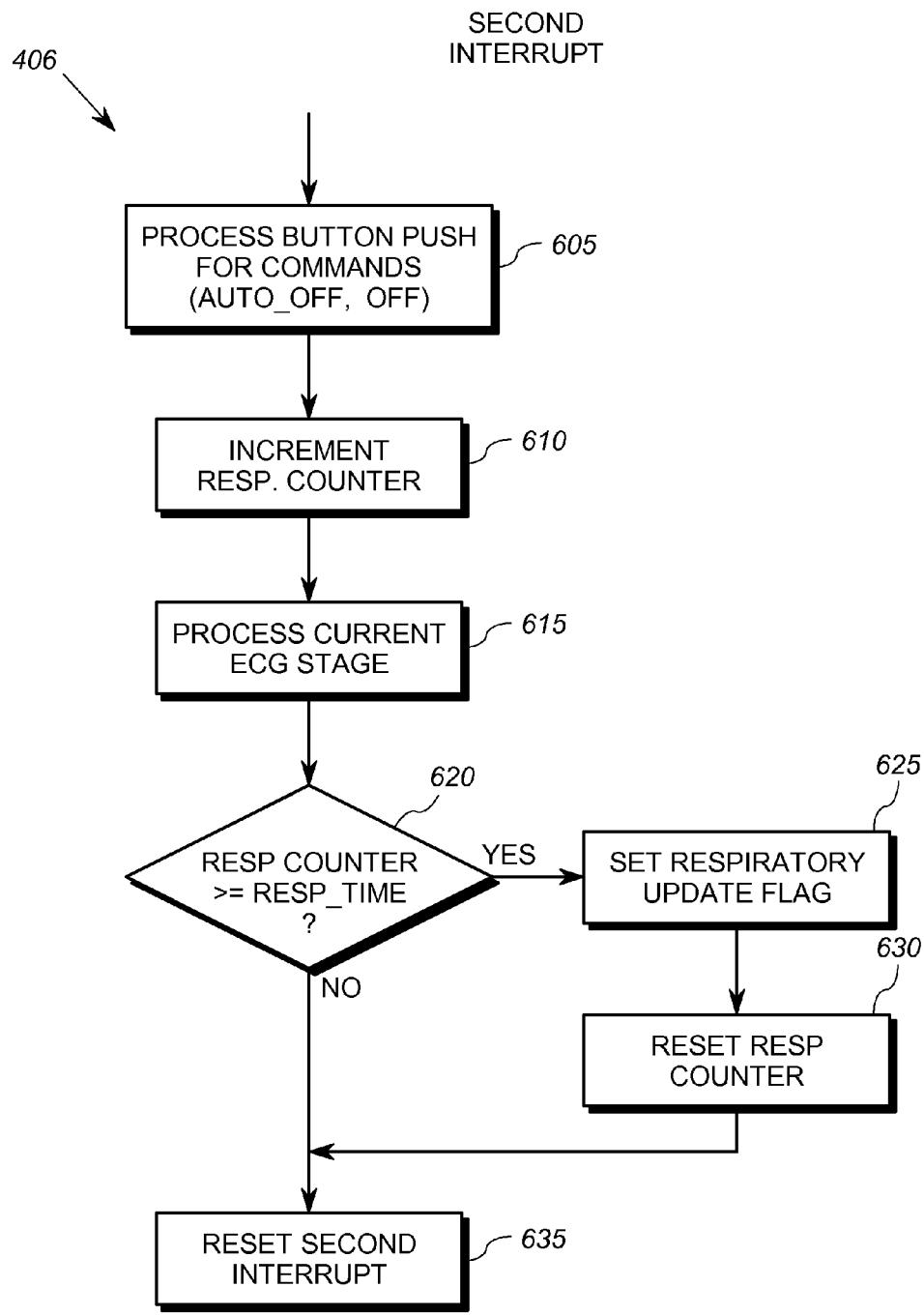
FIG. 6 shows a flow diagram of an exemplary second interrupt routine of the computer program of FIG. 4.

FIG. 6 shows an exemplary set of operations that carry the second interrupt routine 406 of FIG. 4. The flow diagram 406 of FIG. 6 is carried out every millisecond.

Initially, in step 605, the processing device 212 processes the input device 104 for other commands, such as a command for shutting off the cardiac simulator 100. In particular, the processing device 212 is configured by the programming instructions to detect when the input device 104 has been held for three seconds continuously, and to enter the sleep mode (i.e. set the off_flag) responsive to such an occurrence. To this end, the processing device 212 in step 605 maintains (and monitors) a counter for the length of time that the input device 104 is generating an actuation signal (indicating that it is being actuated). The processing device 212 resets the counter if the input device 104 is released, and does not start it again until the input device 104 is again actuated. If this counter ever reaches the amount of time equal to the shut off time (three seconds or 3000 ms), then the processing device 212 sets the off_flag flag, which will be acted upon the next time that step 515 of FIG. 5 is executed. Further detail regarding an exemplary set of operations that may be used to carry out these processes is provided below in connection with FIG. 7.

In any event, it will be appreciated that the single button input device 104 is capable of multiple actions, including turn-on, turn-off, and advancing to the next setting. As will discussed below, the input device 104 may also be used to toggle an "auto-off" feature.

After step 605, the processing device 212 executes step 610. In step 610, the processing device 212 increments the counter resp_counter, which is used to perform the timing of the respiration signals generated in the step 435 discussed above in connection with FIG. 4. The value resp_counter in this embodiment represents the number of milliseconds in the current respiration signal stage. Unlike the ECG stages discussed above, the respiration signal stage in this embodiment is one of forty stages that the entire respiration waveform is evenly divided. The value resp_counter is subsequently processed in step 620, discussed further below. After step 610, the processing device 212 executes step 615.

In step 615, the processing device 212 generates one value of the sequence of digital ECG output values using one of the plurality of mathematic relationships as a function of time. As will be discussed below, a mathematical relationship is defined for each of the stages of the ECG signal. Accordingly, during each execution (i.e. pass) of step 615, the processing device 212 generates an output value using the mathematical relationship(s) corresponding to one of the stages of the ECG signal. The processing device 212 provides the generated output value to the DAC 204 using serial data communication as discussed above in connection with FIG. 2. Further detail regarding the operation of step 615 is provided below in connection with FIGS. 8A and 8B.

After step 615, the processing device 212 executes step 620. In step 620, the processing device 212 determines whether the value of resp_counter exceeds a value resp_time. The value resp_time is inversely proportional to the respiration frequency for the current setting or profile. In this embodiment, the value of resp_time is set equal to:

resp_time=(60,000/resp_freq$_x$)/stages wherein resp_freq$_x$ is the respiration rate (breaths per minute), and stages is the number of stages into which the respiration waveform is broken up. It will be appreciated that 60,000 represents the number of milliseconds in one minute. As discussed above, the respiration waveform is broken into 40 stages in this embodiment. As a consequence, the value stages=40.

In any event, if the processing device 212 determines that resp_counter equals or exceeds resp_time, then the processing device 212 proceeds to step 625. If not, then the processing device 212 proceeds to step 635. In step 625, the processing device 212 sets the resp_update flag and then proceeds to step 630. The resp_update flag is the flag referenced in step 430 of FIG. 4 to determine whether to update the respiration signal output. In step 630, the processing device 212 resets the value of resp_counter. The processing device 212 thereafter proceeds to step 635.

In step 635, the processing device 212 resets the high interrupt flag, and exits the high interrupt routine of FIG. 6.

Further detail regarding the second interrupt routine 406 is provided below in connection with FIGS. 7, 8A and 8B. In particular, FIG. 7 shows in further detail the operations of step 605 of FIG. 6, and FIGS. 8A and 8B show in further detail the operations of step 615 of FIG. 6.

As discussed above, the processing device 212 in step 605 monitors the state of the input device 104 to see if it is being actuated for an extended period of time. In particular, although the actuation of the input device 104 results in a changing of the profile or setting of the cardiac simulator 100 through the operation of the first interrupt routine 404, the user may also hold the input device 104 in the actuated state for an extended period to effectuate other control operations of the cardiac simulator 100.

To this end, the operations of step 605 (i.e. FIG. 7) process the signals for the input device 104 to see if they have been held long enough to change a control parameter of the device 100. For example, in this embodiment, continuous actuation of the input device 104 for two to four seconds can be used to turn off the cardiac simulator 100 (i.e. transition the processing device 212 to sleep mode). In another example, continuous actuation of the input device 104 at start-up for two to four seconds continuously can be used to disable an automatic shutoff feature programmed in the device 100.

Figure 7:
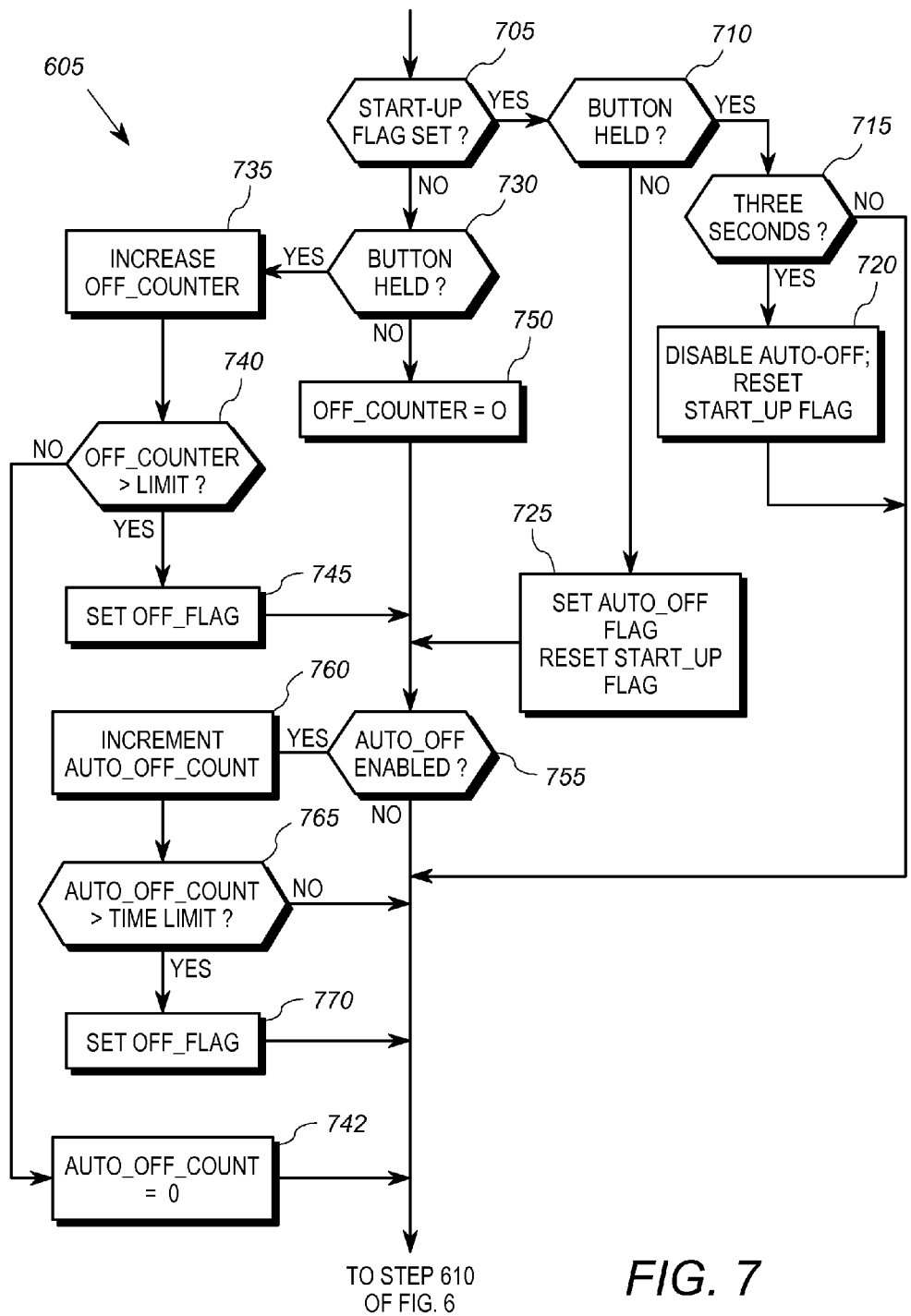
FIG. 7 shows a flow diagram of an exemplary button processing routine of the second interrupt routine of FIG. 6.

Referring now to FIG. 7, in step 705, the processing device 212 determines whether a start up flag start_up is set. The flag start_up is initially set in step 410 of FIG. 4 when the processing device 212 enters the active mode from the sleep mode. If the start_up flag is set, then the processing device 212 proceeds to step 710. If not, then the processing device 212 proceeds to step 730.

Start_Up Flag Set

In step 710, the processing device 212 determines if the input device 104 is currently actuated. If not, then the processing device 212 proceeds to step 725. If so, however, then the processing device 212 performs step 715.

In step 715, the processing device 212 determines whether the input device 104 has been continuously actuated for three seconds. If not, then the processing device 212 has completed the operations of step 605 and proceeds to step 610 of FIG. 6. If, however, the input device 104 has been continuously actuated for three seconds, then the processing device 212 proceeds to step 720. In step 720, the processing device 212 disables the automatic shutoff feature by setting the flag auto_off to 0. In addition in step 720, the processing device 212 resets the flag start_up to 0 and proceeds to step 610 of FIG. 6.

In step 725, which is executed only if the processing device 212 determines that the input device 104 is not actuated in step 710, the processing device 212 sets the flag auto_off to 1 to indicate that the automatic shutoff feature is enabled. This occurs because the input device 104 was not actuated for three continuous seconds at the start up. In addition in step 725, the processing device 212 resets the flag start_up and proceeds to step 755, discussed further below.

Start_Up Flag Not Set

As discussed above, if the processing device 212 determines in step 710 that the start_up flag is not set, then step 730 is processed. In particular, the processing device 212 executes steps 730 to 750 to detect whether the input device 104 is being actuated for an extended time in order to turn off (i.e. enter sleep mode) the cardiac simulator 100. To this end, in step 730, the processing device 212 determines if the input device 104 is currently actuated. If not, then the processing device 212 skips to step 750. If so, however, then the processing device 212 proceeds instead to step 735.

In step 735, the processing device 212 increments a counter off_counter that is representative of how long the input device 104 is continually actuated. After step 735, the processing device 212 proceeds to step 740. In step 740, the processing device 212 determines whether off_counter exceeds a first threshold limit. Preferably the first threshold limit is equivalent to the value off_counter accumulating for two to four seconds. In the present embodiment, because the operations of FIG. 7 are performed every millisecond, the first threshold limit may suitably be 2000 to 4000. If the value off_counter exceeds the first threshold limit, then the processing device 212 proceeds to step 745. If not, then the processing device 212 advances to step 742. In step 742, the processing device 212 resets the counter auto_off_count and then proceeds to step 610 of FIG. 6.

In particular, as will be discussed further below, the auto_off_count is the duration of time that passes without actuation of the input device 104. As also discussed below, the automatic shutoff feature is one in which the device 100 (i.e. the processing device 212) automatically shuts down (enters sleep mode) if no actuation of the input device 104 occurs for an extended period, such as five to sixty minutes. In this embodiment, the duration is fifteen minutes. Step 742 ensures that the counter auto_off_count is reset to zero whenever the input device 104 is actuated.

In any event, referring again to the processing of a forced turn-off via the input device 104, the processing device 212 executes step 745 only if the off_counter value exceeds the first threshold limit. In step 745, the processing device 212 sets the off_flag to 1, which will cause the device 100 to shut down at the next execution of step 415 of FIG. 4. After step 745, the processing device 212 proceeds to step 755. However, it will be appreciated that because the off_flag is already set to 1, the processing device 212 may instead proceed directly to step 610 of FIG. 6.

As discussed above, the processing device 212 performs step 750 if it is determined that the input device 104 is not actuated in step 730. In step 750, the processing device 212 sets the off_counter equal to 0. In other words, because the input device 104 has been released (or remains unactuated), the off_counter must start over from zero, only to restart in the event that the input device 104 is again actuated. After step 750, the processing device 212 proceeds to step 755.

Steps 755 to 770 represent the automatic shut off feature. To this end, in step 755, the processing device 212 determines whether the flag auto_off is set (i.e. auto_off=1). If not, then the automatic shut-off feature has been disabled (see step 720) and the processing device 212 proceeds directly to step 610 of FIG. 6.

If, however, the flag auto_off is set to 1, then the processing device 212 proceeds to step 760. In step 760, the processing device 212 increments the auto_off_count counter and then proceeds to step 765.

In step 765, the processing device 212 determines whether auto_off_count exceeds a second threshold limit. Preferably the second threshold limit is equivalent to the value of auto_off_count accumulating for fifteen minutes. In the present embodiment, because the operations of FIG. 7 are performed every millisecond, the second threshold limit may suitably be 900,000. If the value of auto_off_count exceeds the second threshold limit, then the processing device 212 proceeds to step 770. If not, then the processing device 212 advances to step 610 of FIG. 6. In step 770, the processing device 212 sets the off_flag in the manner discussed above in connection with step 745.

It can be seen from FIG. 7 that a single, two-state input device 104 such as a pushbutton can be used not only to advance the profile or setting as discussed above in connection with FIGS. 1 and 5, but also to change other operating parameters such as disabling an automatic shut-off feature, causing a manual shut-off, and resetting a counter on an activated automation shut-off operation.

Figure 8A:
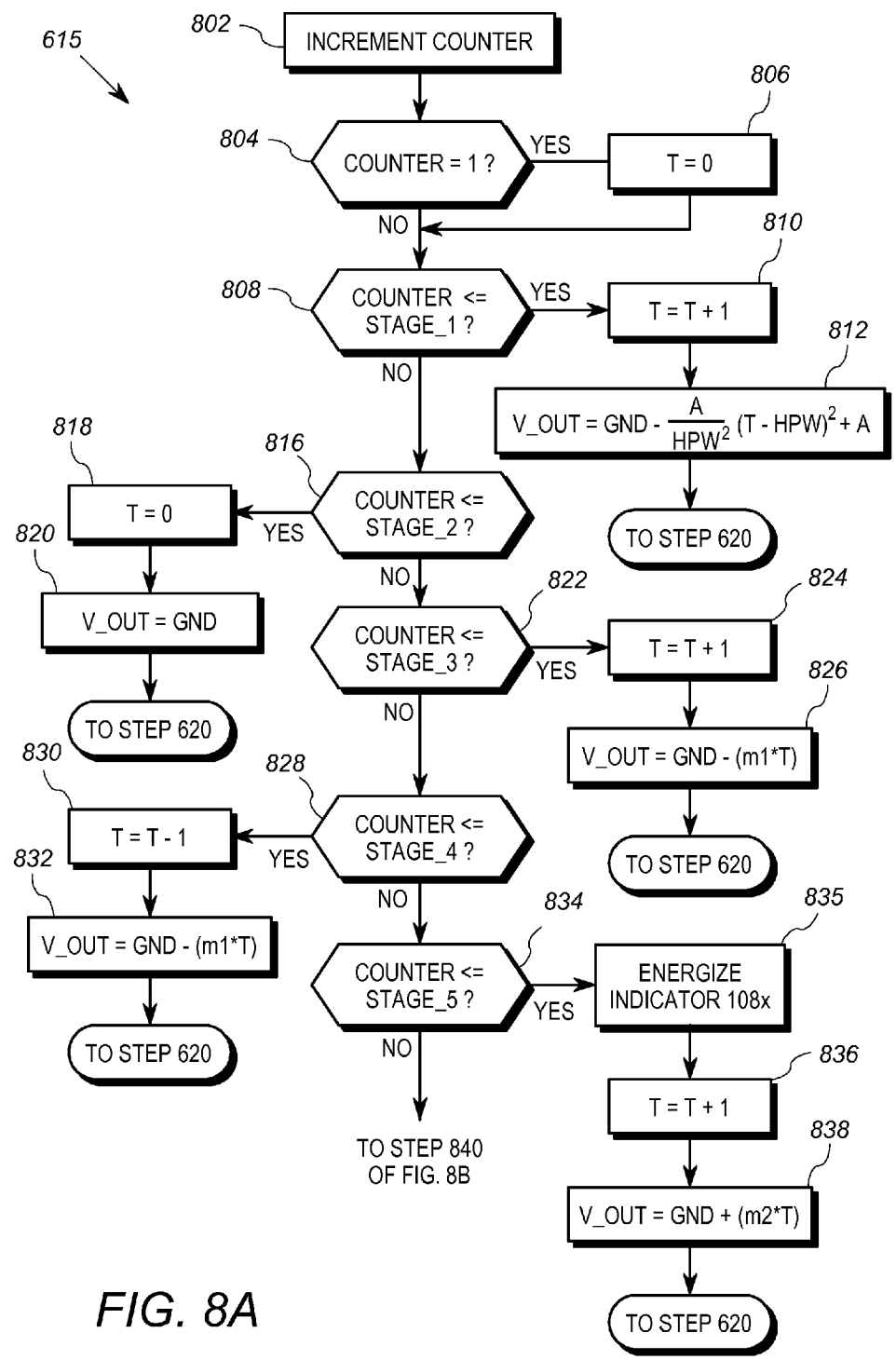
FIGS. 8A and 8B show a flow diagram of an exemplary routine for generating an ECG waveform sample of the second interrupt routine of FIG. 6.
Figure 8B:
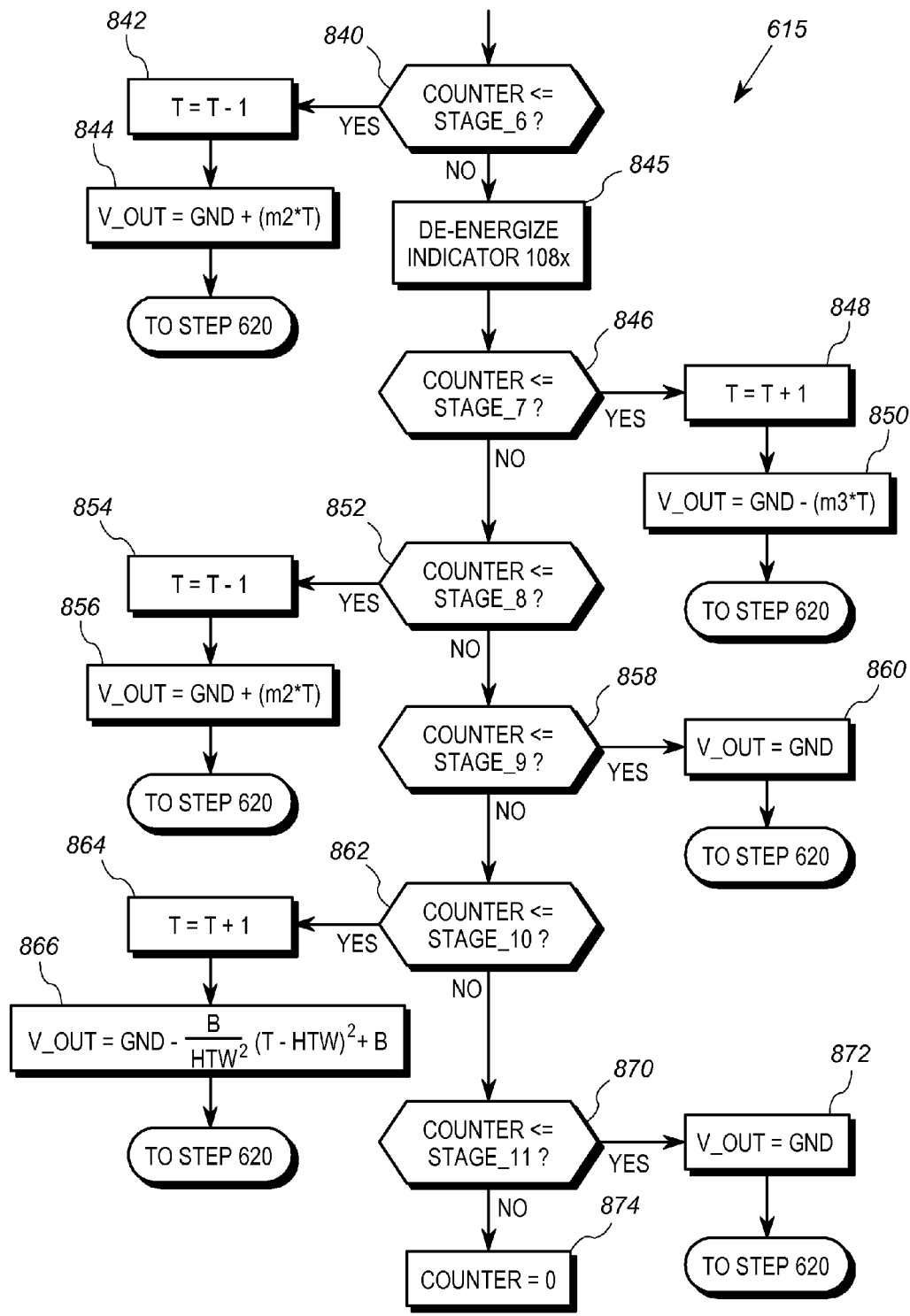

FIGS. 8A and 8B show an exemplary set of operations that may be used to generate an ECG output digital waveform sample for each millisecond of operation of the device 100. In other words, the flow diagram of FIGS. 8A and 8B represent the operations of step 615 of FIG. 6 in further detail. In general, during each pass of the operations of FIGS. 8A and 8B, the processing device 212 generates the digital sample based on one of a plurality of predetermined mathematical relationships. The mathematical relationship that is applied during any particular execution of step 615 is based on where the digital sample falls within the ECG waveform 300. As will be discussed below, the value counter indexes the position of the current digital sample within the larger ECG waveform 300. In this embodiment, each value of counter relates to one millisecond of the ECG waveform 300.

Referring now to FIG. 8A, in step 802, the processing device 212 first increments the value counter to advance to the current position (within the ECG waveform 300) of the digital sample to be generated.

Thereafter, in step 804, the processing device 212 determines whether the present value of counter=1. In other words, the processing device 212 determines whether a new ECG waveform 300 is starting. If not, then the processing device 212 proceeds directly to step 808. If not, however, then the processing device first proceeds to step 806 to set a time variable T equal to zero. After step 806, the processing device 212 proceeds to step 808.

In step 808, the processing device 212 determines whether counter is less than or equal to the counter limit stage_1 for stage 1 of the ECG waveform 300. As discussed above in connection with step 515 FIG. 5, the value stage_1 corresponds to the duration of the ECG waveform 300 up to an including the end of the P-Wave 302. If counter<stage_1, then the processing device 212 proceeds to step 810 to generate the current digital sample in accordance with the mathematical relationship corresponding to the P-wave 302. If not, then the processing circuit 212 skips to step 816.

P-Wave

In step 810, the processing device 212 increments the time-based counter T, and then proceeds to step 812. In step 812, the processing device 212 performs an interim non-linear (i.e. second order) equation to generate the value V_OUT, which corresponds to (and defines) the curve of the P-Wave 302. This calculation is as follows:

$$V\_OUT = GND - \frac{A}{HPW^2}(T - HPW)^2 + A$$

where GND is the digital value corresponding to ground or zero volts, HPW is half of the width of the P-wave determined in step 515, discussed above, and A is a scaling constant related to the scale employed by the processing device 212 and the DAC 204. In this embodiment, the value A is the maximum amplitude of the P-wave 302 (See FIG. 3). It will be appreciated that the above-calculation for V_OUT may be split into several sub-calculations if desirable.

In this embodiment, the value of A is 100, which corresponds to 100 mV. It will be appreciated that numbers other than 100 may be used, depending on the scale of digital values employed by the DAC 204, and the desired maximum height of the P-Wave 302 in the generated output signal.

In any event, the processing device 212 provides the generated output sample V_OUT to the DAC 204 as discussed above in connection with FIG. 2. After generating and outputting the digital output sample V_OUT, the processing device 212 has completed step 615 of FIG. 6 and may proceed directly to step 620 of FIG. 6.

Thus, it can be seen that steps 810 to 814 define a mathematical relationship that forms a curve over the course of several samples as a function of time, represented as the variable T.

PQ-Rest

In step 816, the processing device 212 determines whether counter is less than or equal to the counter limit stage_2 for stage 2 of the ECG waveform 300. As discussed above in connection with step 515 FIG. 5, the value stage_2 corresponds to the duration of the ECG waveform 300 up to an including the end of the PQ-Rest 304. If counter<stage_2, then the processing device 212 proceeds to step 818 to generate the current digital sample V_OUT in accordance with the mathematical relationship corresponding to the PQ-rest 304. If not, then the processing circuit 212 skips to step 822.

In step 818, the processing device 212 sets the counter T to 0. Thereafter, in step 820, the processing device 212 generates the output digital value V_OUT using the following equation:

$V\_OUT=GND$,

The processing device 212 provides the generated output sample V_OUT to the DAC 204 as discussed above in connection with FIG. 2. After generating and outputting the digital output sample V_OUT, the processing device 212 has completed step 615 of FIG. 6 and may proceed directly to step 620 of FIG. 6.

Thus, it can be seen that steps 818 to 820 define a mathematical relationship that forms a constant value GND over the course of several samples. The counter T is not incremented because the relationship is, effectively, not time-variant.

Stage 3 Portion of QRS Complex

In step 822, the processing device 212 determines whether counter is less than or equal to the counter limit stage_3 for stage 3 of the ECG waveform 300. As discussed above in connection with step 515 FIG. 5, the value stage_3 corresponds to the duration of the ECG waveform 300 up to an including the end of a first portion 306a of the QRS complex. This first portion 306a is the first half of the Q-wave 306a, 306b of FIG. 3. If counter<stage_3, then the processing device 212 proceeds to step 824 to generate the current digital sample in accordance with the mathematical relationship corresponding to the stage 3 portion of the QRS complex. If not, however, then the processing circuit 212 skips to step 828.

In step 824, the processing device 212 increments the time-based counter T, and then proceeds to step 826. In step 826, the processing device 212 determines the value V_OUT based on a linear calculation as a function of time. In this case, the value of time is represented as the incremented value of T. The processing device 212 calculates V_OUT using the following calculation:

$$V\_OUT=GND-(m1*T)$$

where m1 is the absolute value of the slope of the linear portion 306a. It can be seen that the true slope of the line as a function of T is negative, or in other words, the slope of the linear portion 306a is −m1.

In any event, the processing device 212 provides the generated output sample V_OUT to the DAC 204 as discussed above in connection with FIG. 2. After generating and outputting the digital output sample V_OUT, the processing device 212 has completed step 615 of FIG. 6 and may proceed directly to step 620 of FIG. 6.

Thus, it can be seen that steps 824 and 826 define a mathematical relationship that forms a line over the course of several samples as a function of time, represented as the variable T.

Stage 4 Portion of QRS Complex

In step 828, the processing device 212 determines whether counter is less than or equal to the counter limit stage_4 for stage 4 of the ECG waveform 300. As discussed above in connection with step 515 FIG. 5, the value stage_4 corresponds to the duration of the ECG waveform 300 up to an including the end of the second portion 306b of the QRS complex. This second portion 306b is the second half of the Q-wave 306a, 306b of FIG. 3. If counter<stage_4, then the processing device 212 proceeds to step 830 to generate the current digital sample in accordance with the mathematical relationship corresponding to the stage 4 portion of the QRS complex. If not, however, then the processing circuit 212 skips to step 834.

In step 830, the processing device 212 decrements the time-based counter T, and then proceeds to step 832. In step 832, the processing device 212 determines the value V_OUT based on a linear calculation as a function of time. In this case, the value of time is represented as the decremented value of T. The processing device 212 calculates V_OUT using the following calculation:

$$V\_OUT=GND-(m1*T)$$

where m1 is the absolute value of the slope of the linear portion 306b. It will be appreciated that the value m1 is the absolute value of the slope in both portions 306a, 306b of the Q-wave in this embodiment. However, it will be appreciated that in the second portion 306b, the true slope of the line as a function of time is positive. In particular, because T is decremented as function of time, the sign of the slope is reversed with respect to the value T. Thus, while the slope of the V_OUT calculation shown above is −m1, the decrementing of T with respect to time causes the slope of the V_OUT calculation with respect to time to be simply +m1.

In any event, the processing device 212 provides the generated output sample V_OUT to the DAC 204 as discussed above in connection with FIG. 2. After generating and outputting the digital output sample V_OUT, the processing device 212 has completed step 615 of FIG. 6 and may proceed directly to step 620 of FIG. 6.

Thus, it can be seen that steps 830 and 832 also define a mathematical relationship that forms a positive-sloped line over the course of several samples as a function of time.

Stage 5 Portion of QRS Complex

In step 834, the processing device 212 determines whether counter is less than or equal to the counter limit stage_5 for stage 5 of the ECG waveform 300. As discussed above in connection with step 515 FIG. 5, the value stage_5 corresponds to the duration of the ECG waveform 300 up to an including the end of the up-sloped portion of the R-wave 308 of FIG. 3. If counter<stage_5, then the processing device 212 proceeds to step 835. If not, however, then the processing circuit 212 skips to step 840.

In step 835, prior to generating the current digital sample V_OUT, the processing device 212 first generates an output voltage to energize or illuminate the indicator 108a-108f corresponding to the current profile (see Table 1). As will be seen below, the processing device 212 energizes the indicator 108x corresponding to the current profile x during the stages 5 and 6 (i.e. portions 308 and 310 of the QRS complex) of the waveform 300. At other times, the indicator 108x is not energized. Accordingly, the indicator 108x blinks on and off in synchronization with the portions 308 and 310 while the cardiac simulator 100 is in the profile x. This allows the current indicator 108x to blink at the heart rate corresponding to the profile x, since the portions 308 and 310 occur only once per ECG waveform 300.

In any event, after step 835, the processing device 212 proceeds to step 836 to generate the current digital sample in accordance with the mathematical relationship corresponding to the stage 5 portion of the QRS complex.

In step 836, the processing device 212 increments the time-based counter T, and then proceeds to step 838. In step 838, the processing device 212 determines the value V_OUT based on a linear calculation as a function of time. In this case, the value of time is represented as the incremented value of T. The processing device 212 calculates V_OUT using the following calculation:

$$V\_OUT=GND+(m2*T)$$

where m2 is the slope of the linear portion 308. In this embodiment, the absolute value of m2 is greater than the absolute value of the slope m1 of the Q-wave portions 306a, 306b. Thus, the slope of the V_OUT calculation of the up-sloped portion of the R-wave 308 is m2.

In any event, the processing device 212 provides the generated output sample V_OUT to the DAC 204 as discussed above in connection with FIG. 2. After generating and outputting the digital output sample V_OUT, the processing device 212 has completed step 615 of FIG. 6 and may proceed directly to step 620 of FIG. 6.

Thus, it can be seen that steps 836 and 838 define a mathematical relationship that forms a line over the course of several samples as a function of time.

Stage 6 Portion of QRS Complex

In step 840, the processing device 212 determines whether counter is less than or equal to the counter limit stage_6 for stage 6 of the ECG waveform 300. As discussed above in connection with step 515 FIG. 5, the value stage_6 corresponds to the duration of the ECG waveform 300 up to an including the end of the down-sloped portion of the R-wave 310 of FIG. 3. If counter<stage_6, then the processing device 212 proceeds to step 842 to generate the current digital sample in accordance with the mathematical relationship corresponding to the stage 6 portion of the QRS complex. If not, however, then the processing circuit 212 skips to step 845.

In step 842, the processing device 212 decrements the time-based counter T, and then proceeds to step 844. In step 844, the processing device 212 determines the value V_OUT based on a linear calculation as a function of time. In this case, the value of time is represented as the decremented value of T. The processing device 212 calculates V_OUT using the following calculation:

$$V\_OUT = GND + (m2*T)$$

where m2 is the absolute value of slope of the linear portion 310, which in this embodiment is the same as the absolute value of the slope of the linear portion 308. It will be appreciated that the true slope of the line of stage 6 is negative. In particular, because T is decremented as a function of time, the sign of the slope is reversed with respect to the value T. Thus, while the slope of the V_OUT calculation is m2, the decrementing of T with respect to time causes the slope of the V_OUT calculation with respect to time to be inverted to −m2.

In any event, the processing device 212 provides the generated output sample V_OUT to the DAC 204 as discussed above in connection with FIG. 2. After generating and outputting the digital output sample V_OUT, the processing device 212 has completed step 615 of FIG. 6 and may proceed directly to step 620 of FIG. 6.

Thus, it can be seen that steps 842 and 844 define a mathematical relationship that forms a line over the course of several samples as a function of time.

Stage 7 Portion of QRS Complex

In step 845, the processing device 212 turns off or de-energizes the indicator 108x corresponding to the current profile x. Accordingly, the current profile indicator 108x is blinked off after stage 6 has been completed. The processing device then executes step 846. In step 846, the processing device 212 determines whether counter is less than or equal to the counter limit stage_7 for stage 7 of the ECG waveform 300. As discussed above in connection with step 515 FIG. 5, the value stage_7 corresponds to the duration of the ECG waveform 300 up to an including the end of a down-sloped portion 312a of the S-wave of FIG. 3. If counter<stage_7, then the processing device 212 proceeds to step 848 to generate the current digital sample in accordance with the mathematical relationship corresponding to the stage 7 portion of the QRS complex. If not, however, then the processing circuit 212 skips to step 852.

In step 848, the processing device 212 increments the time-based counter T, and then proceeds to step 850. In step 850, the processing device 212 determines the value V_OUT based on a linear calculation as a function of time. In this case, the value of time is represented as the value of T. The processing device 212 calculates V_OUT using the following calculation:

$$V\_OUT = GND - (m3*T)$$

where m3 is the absolute value of slope of the linear portion 310. It will be appreciated that the true slope of the line as a function of time is negative, or −m3. In this embodiment, the slope m3 is greater than the absolute value of the slope m1 of the Q-wave portions 306a, 306b. Thus, the S-wave portions 312a, 312b are larger than the Q-wave portions 306a, 306b, as in a normal ECG wave.

In any event, the processing device 212 provides the generated output sample V_OUT to the DAC 204 as discussed above in connection with FIG. 2. After generating and outputting the digital output sample V_OUT, the processing device 212 has completed step 615 of FIG. 6 and may proceed directly to step 620 of FIG. 6.

Stage 8 Portion of QRS Complex

In step 852, the processing device 212 determines whether counter is less than or equal to the counter limit stage_8 for stage 8 of the ECG waveform 300. As discussed above in connection with step 515 FIG. 5, the value stage_8 corresponds to the duration of the ECG waveform 300 up to an including the end of the up-sloped portion 312b of the S-wave as shown in FIG. 3. If counter<stage_8, then the processing device 212 proceeds to step 854 to generate the current digital sample in accordance with the mathematical relationship corresponding to the stage 8 portion of the QRS complex. If not, however, then the processing circuit 212 skips to step 858.

In step 854, the processing device 212 decrements the time-based counter T, and then proceeds to step 856. In step 856, the processing device 212 determines the value V_OUT based on a linear calculation as a function of time. In this case, the value of time is represented as the decremented value of T. The processing device 212 calculates V_OUT using the following calculation:

$$V\_OUT = GND - (m3*T)$$

It will be appreciated that the true slope of the line as a function of time is positive, or m3. The slope of the line is positive as a function of time because although the slope in the V_OUT equation above is −m3, the variable T is decremented as a function of time.

In any event, the processing device 212 provides the generated output sample V_OUT to the DAC 204 as discussed above in connection with FIG. 2. After generating and outputting the digital output sample V_OUT, the processing device 212 has completed step 615 of FIG. 6 and may proceed directly to step 620 of FIG. 6.

ST-Rest

In step 858, the processing device 212 determines whether counter is less than or equal to the counter limit stage_9 for stage 9 of the ECG waveform 300. As discussed above in connection with step 515 FIG. 5, the value stage_9 corresponds to the duration of the ECG waveform 300 up to an including the end of the ST-rest 314 as shown in FIG. 3. If counter<stage_9, then the processing device 212 proceeds to step 860 to generate the current digital sample V_OUT in accordance with the mathematical relationship corresponding to the ST-rest 314. If not, then the processing circuit 212 skips to step 862.

In step 860, the processing device 212 generates the output digital value V_OUT using the following equation:

$$V\_OUT = GND.$$

The processing device 212 provides the generated output sample V_OUT to the DAC 204 as discussed above in connection with FIG. 2. After generating and outputting the digital output sample V_OUT, the processing device 212 has completed step 615 of FIG. 6 and may proceed directly to step 620 of FIG. 6.

Thus, it can be seen that step 860 define a mathematical relationship that forms a constant value GND over the course of several samples. The counter T is not incremented because the relationship is, effectively, not time-variant.

T-Wave

In step 862, the processing device 212 determines whether counter is less than or equal to the counter limit stage_10 for stage 10 of the ECG waveform 300. As discussed above in connection with step 515 FIG. 5, the value stage_10 corresponds to the duration of the ECG waveform 300 up to an including the end of the T-wave 316. If counter<stage_10, then the processing device 212 proceeds to step 864 to generate the current digital sample V_OUT in accordance with the mathematical relationship corresponding to the T-wave 316. If not, then the processing circuit 212 skips to step 870.

In step 864, the processing device 212 increments the time-based counter T, and then proceeds to step 866. In step 866, the processing device 212 performs an interim non-linear (i.e. second order) equation to generate an interim value X, which corresponds to (and defines) the curve of the T-Wave 316. This calculation is as follows:

$$V\_OUT = GND - \frac{B}{HTW^2}(T - HTW)^2 + B$$

where HTW is half of the width of the T-wave determined in step 515, discussed above, and B is a constant that defines the magnitude of the T-wave portion 316. In this embodiment, B is 200 or in any event twice that of the magnitude constant A of the P-wave portion 302. It will be appreciated that numbers other than 200 may be used, depending on the scale of digital values employed by the DAC 204, and the desired maximum height of the T-wave portion 316. However, in this embodiment, it will be appreciated that the number selected value 200 is twice that used as the maximum height of the P-wave 302, discussed further above.

In any event, the processing device 212 provides the generated output sample V_OUT to the DAC 204 as discussed above in connection with FIG. 2. After generating and outputting the digital output sample V_OUT, the processing device 212 has completed step 615 of FIG. 6 and may proceed directly to step 620 of FIG. 6.

Thus, it can be seen that steps 864 to 868 define a mathematical relationship that forms a curve over the course of several samples as a function of time, represented as the variable T.

End-Rest

In step 870, the processing device 212 determines whether counter is less than or equal to the counter limit stage__11 for stage 11 of the ECG waveform 300. As discussed above in connection with step 515 FIG. 5, the value stage__11 corresponds to the duration of the ECG waveform 300 up to an including the end of the end-rest 318. If counter<stage__11, then the processing device 212 proceeds to step 872 to generate the current digital sample V_OUT in accordance with the mathematical relationship corresponding to the end-rest 318. If not, then the processing circuit 212 proceeds to step 874.

In step 872, the processing device 212 generates the output digital value V_OUT using the following equation:

$$V\_OUT=GND,$$

The processing device 212 provides the generated output sample V_OUT to the DAC 204 as discussed above in connection with FIG. 2. The counter T is not incremented because the relationship is, effectively, not time-variant. After generating and outputting the digital output sample V_OUT, the processing device 212 has completed step 615 of FIG. 6 and may proceed directly to step 620 of FIG. 6.

ECG Waveform Complete

Step 874 is reached once the value of counter exceeds the total duration (in milliseconds in this embodiment) of the ECG waveform 300. Accordingly, the processing device 212 in step 874 resets the value of counter to 0. As a consequence, the next time that step 615 is executed, the processing device 212 will generate the beginning of a new ECG waveform.

Thus, in general, in step 615 of FIG. 6, shown in FIGS. 8A and 8B, the processing device 212 generates a single ECG waveform sample generated in accordance with one of a plurality of mathematical relationships, wherein each mathematical relationship is associated with a stage of the ECG waveform 300. In this embodiment, some mathematical relationships include a constant value as a function of time, another set of mathematical relationships define a sloped line, and yet another set of mathematical relationships define curves. The processing circuit 212 employs the mathematical relationship in sequence to form a sequence of samples having the general shape of the ECG waveform 300 of FIG. 3, in a repeating pattern.

It will be appreciated that by changing the values of one or more of stage__1, stage__2, ... stage__11, the duration of the ECG waveform of the output test signal, and hence the effective BPM or pulse rate, may be altered. Table 2, step 510 and Table 3, discussed further above, illustrate how the values stage__1, stage__2, ... stage__11 are altered to generate different BPM values for the six profiles of the present embodiment. It will further be appreciated that because of the nature of the use of mathematical relationships (as opposed to stored sample values), many parameters (in addition to duration or BPM) of the ECG test signal may be altered. For example, the slopes of the Q-wave, R-wave and S-wave may readily be altered by changing m1, m2, m3. Similarly, the heights of the P-wave and T-wave may be altered.

As discussed in FIG. 4, the processing device 435 also generates output digital signals that cause the potentiometer 205 to effectively modulate a respiration signal onto the ECG signal generated by the DAC 204. FIG. 9 shows in further detail the operations of 435 of FIG. 4, wherein the respiration signal is updated. As discussed above, the respiration signal is modulated onto the ECG signal output of the DAC 204 using a variable resistance connected to the analog output circuit 206. This variable resistance is provided by the potentiometer 205. FIG. 9 shows how the processing circuit 212 generates signals that control the output resistance of the potentiometer 205 to modulate the respiration signal onto the ECG signal.

In general, the respiration cycle is divided into "stages". The value resp_stage is the index of the respiration cycle stages. Each execution of step 435 of FIG. 4, and hence the flow diagram of FIG. 9, corresponds to a single stage of the respiration cycle. In this embodiment, the respiration signal is essentially a (sampled) trapezoidal-shaped wave. Each resp_stage value represents a single "sample" of the respiration signal. Thus, each time the operations of FIG. 9 occur, they occur for a single value of resp_stage.

In this embodiment, each respiration cycle or waveform comprises forty stages. However, it will be appreciated that more or fewer stages may be employed.

Referring now to FIG. 9 in particular, the processing device 212 in step 902 first resets the respiratory update flag to 0. This occurs at the execution of the flow diagram of FIG. 9 to ensure that a proper amount of time passes before step 435 is executed again in FIG. 4. The processing device 212 thereafter proceeds to step 905.

In step 905, the processing device 212 first determines whether the value of a value resp_stage is less than 16. If the value of resp_stage is less than 16, then the processing device 212 proceeds to step 910. If not, then the processing device 212 skips to step 915.

In step 910, the processing device 212 generates one or more output commands that cause the potentiometer 205 to decrease the resistance at both connections P0W and P1W by one step. The processing device 212 causes the output command(s) to be provided to the potentiometer 205 in the manner described above in connection with FIG. 2. Responsive to receive such command(s), the potentiometer decrements the resistance from P0W to ground by 117 ohms, and decrements the resistance from P1W to ground by 117 ohms.

This act effectively modulates the test signal provide across outputs 106a-106e of the device. Thus, each time step 435 is executed while resp_stage is less than 16, the resistances from potentiometer outputs P0W and P1W to ground decrease. After step 910, the processing device 212 skips down to step 950.

In step 915, which is executed because the value of resp_stage was determined to be 16 or more, the processing device 212 determines whether the value of resp_stage is less than 20. If so, the processing device 212 does not provide any output, but rather skips to step 950. Thus, for the values of resp_stage from 16-19, no change occurs in the resistances from P0W and P1W to ground.

However, if it is determined that the value of resp_stage is not less than 20, then the processing device 212 executes step 920. In step 920, the processing device 212 determines whether the value of a value resp_stage is less than 36. If the value of resp_stage is less than 36, then the processing device 212 proceeds to step 925. If not, then the processing device 212 skips to step 930.

In step 925, the processing device 212 generates one or more output commands that cause the potentiometer 205 to increase the resistance at both connections P0W and P1W by one step. The processing device 212 causes the output command(s) to be provided to the potentiometer 205 in the manner described above in connection with FIG. 2. Responsive to receive such command(s), the potentiometer increases the resistance from P0W to ground by 117 ohms, and increases the resistance from P1W to ground by 117 ohms. The processing device 212 thereafter proceeds to step 950.

In step 930, which is executed if the value of resp_stage is not less than 36, the processing device 212 determines whether the value of resp_stage is less than 39. If so, the processing device 212 does not provide any output, but rather skips to step 950. Thus, for the values of resp_stage from 36-38, no change occurs in the resistances from P0W and P1W to ground.

However, if it is determined that the value of resp_stage is not less than 39, then the respiration cycle is complete and the processing device 212 executes step 935. In step 935, the processing device 212 resets the value of resp_stage to zero. Thus, upon the next execution of the flow diagram of FIG. 9, the respiration cycle starts over. After step 935, the processing device proceeds to step 940.

In step 940, the processing device 212 resets the potentiometer 205 to the starting resistances. This occurs at the end of each respiration cycle to ensure that resistance values always start from the same value at the first resp_stage. After step 940, the processing device 212 proceeds to step 415 of FIG. 4, as discussed further above.

In step 950, which is reached anytime that resp_stage is less than 39, the processing device 212 increments resp_stage, and the operations of step 435 are complete. The processing circuit 212 thereafter proceeds to step 415 of FIG. 4, as discussed further above.

Thus, it can be seen that the signals generated in sequence by the processing device 212 over the course of 40 executions of the operations of FIG. 9 cause the resistances form P0W and P1W to ground to have the general shape, over time, as that of a sampled trapezoid. These resistances form the modulation of the respiratory signal onto the ECG signal.

It will be appreciated that while the use of a plurality of mathematical relationships as a function of time to generate multiple ECG waveforms provides certain power and material savings over the storage of multiple waveform on a sample-by-sample basis, such savings are nevertheless beneficial even if some waveforms are stored on this basis. For example, in one embodiment, the device described herein is enhanced by added specialized arrhythmia ECG signals, which are stored on a sample by sample basis in memory. While the sample-by-sample storage requires more memory, the overall memory usage and associated costs are nevertheless reduced by the use of the plurality of mathematical relationships to form many or most of the ECG waveforms.

It will further be appreciated that the use of the plurality of mathematical relationships provides a parameterized structure that can easily be modified or adjusted. For example, the values of A, B, m1, m2, m3 and the various Stage__1, Stage__2, etc. values may be adjusted to modify the waveform as desired, via additional programming.

It will be appreciated that the above described embodiments are merely exemplary, and that those of ordinary skill in the art may readily devise their own modifications and implementations that incorporate the principles of the present invention and fall within the spirit and scope thereof.

We claim:

1. A cardiac signal generator, comprising:
   a portable housing;
   a memory storing programming instructions, said programming instructions including instructions defining a plurality of mathematical relationships;
   a processing device configured to execute said programming instructions to:
   generate a sequence of output values at least in part by calculating each of a set of the output values using at least one of the plurality of mathematic relationships as a function of time, wherein said sequence of output values defines a sampled waveform output simulating an ECG signal and having linear portions and at least one curved portion, and
   provide the sequence of output values at an output;
   a digital to analog converter operably coupled to receive the sequence of output values from the output, the digital to analog converter configured to generate an electrical signal having a waveform corresponding to the sampled waveform output;
   at least one or more analog outputs operably coupled to the digital to analog converter.

2. The cardiac signal generator of claim 1, wherein the processing device is further configured to generate the sequence of values to include, in sequence, a first curved portion, a positive-slope linear portion, and a negative-slope linear portion.

3. The cardiac signal generator of claim 2, wherein the processing device is further configured to generate the sequence of values to include a first flat portion between the first curved portion and the positive-slope linear portion.

4. The cardiac signal generator of claim 3, wherein the processing device is further configured to generate the sequence of values to include another negative-slope linear portion between the first flat portion and the positive-slope linear portion.

5. The cardiac signal generator claim 1, wherein the processing device is further configured to generate the sequence of values to include, in sequence, a first curved portion, a first flat portion, a first negative-slope linear portion, a first positive-slope linear portion, a second negative-slope linear portion, and a second positive-slope linear portion.

6. The cardiac signal generator of claim 5, wherein the processing device is further configured to:
   generate the first curved portion of sequence of values using a first relationship as function of a counter value;

generate the first flat portion of the sequence of values using a second relationship;

generate the first negative-slope linear portion of the sequence of values using a third relationship as a function of the counter value; and generate the first positive-slope linear portion of the sequence of values using a fourth relationship as a function of the counter value.

7. The cardiac signal generator of claim 1, further comprising a digitally-controlled potentiometer operably coupled to the analog output, and wherein the processing device is further configured to provide digital control signals corresponding to a simulated respiration pattern to the digitally-controlled potentiometer.

8. The cardiac signal generator of claim 1, wherein the first sequence of output values defines a sampled waveform output simulating a repeating ECG waveform, the ECG waveform including an S-wave, an R-wave and a T-wave.

9. The cardiac signal generator of claim 8, wherein the processing device is configured to execute said programming instructions to:

generate output values simulating the S-wave using a first of the plurality of mathematic relationships as a function of time, and generate output values simulating the R-wave using at least a second of the plurality of mathematical relationships as a function of time.

10. The cardiac signal generator of claim 9, wherein the first of the plurality of mathematical relationships defines a curve.

11. A cardiac signal generator, comprising:

a memory storing programming instructions, said programming instructions including instructions defining a plurality of mathematical relationships;

a processing device configured to execute said programming instructions to:

generate a first sequence of output values defining a sampled waveform output simulating an ECG signal and having linear portions and at least one curved portion, and provide the first sequence of output values at a first output;

generate a second sequence of output values defining a sampled waveform output simulating a respiration signal;

provide the second sequence of output values at a second output;

a digital to analog converter operably coupled to receive the first sequence of output values from the output, the digital to analog converter configured to generate an electrical signal having a waveform corresponding to the sampled waveform output;

a potentiometer operably coupled to receive the second sequence of output values, the potentiometer configured to provide a variable resistance based on the second sequence of output values;

at least one or more analog outputs operably coupled to the digital to analog converter and the potentiometer.

12. The cardiac signal generator of claim 11, wherein the analog outputs are configured to provide an output signal comprising the simulated respiration signal superimposed on the simulated ECG signal.

13. The cardiac signal generator of claim 11, wherein the analog outputs include a resistive network operably coupled to the variable resistance of the potentiometer.

14. The cardiac signal generator of claim 11, wherein the processing device is configured to execute said programming instructions to generate the first sequence of output values using a plurality of mathematic relationships as a function of time.

15. The cardiac signal generator of claim 11, wherein the first sequence of output values defines a sampled waveform output simulating a repeating ECG waveform, the ECG waveform including an S-wave, an R-wave and a T-wave.

16. The cardiac signal generator of claim 11 further comprising a portable housing and a battery, wherein the battery is operably coupled to provide operating power to the processing device, the digital to analog converter, and the potentiometer.

17. The cardiac signal generator of claim 11, wherein the processing device is further configured to generate the first sequence of values to include, in sequence, a first curved portion, a positive-slope linear portion, and a negative-slope linear portion.

18. The cardiac signal generator of claim 17, wherein the sampled waveform output simulating the respiration signal comprises a sampled trapezoid-shaped waveform.

19. The cardiac signal generator of claim 11, wherein the sampled waveform output simulating the respiration signal comprises a sampled trapezoid-shaped waveform.

20. The cardiac signal generator of claim 1, wherein the memory stores at least a first slope value; and the processing device is configured to execute said programming instructions to calculate each of the set of output values using a value representative of time multiplied by the first slope value.

21. The cardiac signal generator of claim 20, wherein the memory stores at least a second slope value; and the processing device is configured to execute said programming instructions to calculate each of another set of the output values using the value representative of time multiplied by the second slope value.

* * * * *